(12) United States Patent
Bai et al.

(10) Patent No.: US 11,166,690 B2
(45) Date of Patent: Nov. 9, 2021

(54) NOISE AND ARTIFACT REDUCTION FOR IMAGE SCATTER CORRECTION

(71) Applicant: Accuray, Inc., Sunnyvale, CA (US)

(72) Inventors: Chuanyong Bai, Solon, OH (US); Zhicong Yu, Highland Hts., OH (US); Amit Jain, Solon, OH (US); Daniel Gagnon, Twinsburg, OH (US)

(73) Assignee: Accuray, Inc., Sunnyvale, CA (US)

( * ) Notice: Subject to any disclaimer, the term of this patent is extended or adjusted under 35 U.S.C. 154(b) by 0 days.

(21) Appl. No.: 16/823,560

(22) Filed: Mar. 19, 2020

(65) Prior Publication Data

US 2021/0290194 A1 Sep. 23, 2021

(51) Int. Cl.
*A61B 6/00* (2006.01)
*G01N 23/201* (2018.01)
(Continued)

(52) U.S. Cl.
CPC ............ *A61B 6/5282* (2013.01); *A61B 6/032* (2013.01); *A61B 6/4085* (2013.01);
(Continued)

(58) Field of Classification Search
CPC ............ G01N 2223/423; G01N 23/04; G01N 2223/419; G01N 23/046; G01N 2223/076; G01N 23/223; G01N 2223/505; G01N 2223/108; G01N 23/2255; G01N 23/041; G01N 2223/401; G01N 23/044; G01N 23/083; G01N 23/20066; G01N 2223/045; G01N 2223/507; G01N 23/20008;
(Continued)

(56) References Cited

U.S. PATENT DOCUMENTS

| 4,190,773 A | 2/1980 | Braden et al. |
| 5,615,279 A | 3/1997 | Yoshioka et al. |

(Continued)

FOREIGN PATENT DOCUMENTS

| DE | 102006007058 A1 | 7/2007 |
| EP | 1062914 A1 | 12/2000 |

(Continued)

OTHER PUBLICATIONS

Clackdoyle, et al.. Data consistency conditions for truncated fanbeam and parallel projections, Med Phys. Feb. 2015, pp. 831-845, vol. 42, No. 2.

(Continued)

*Primary Examiner* — Irakli Kiknadze
(74) *Attorney, Agent, or Firm* — Calfee, Halter & Griswold LLP

(57) ABSTRACT

An imaging apparatus and associated methods are provided to receive measured projection data in a primary region and correct for scatter by processing the imaging data as two separate components: non-scatter-corrected data and scatter-only data. Separate image processing (e.g., reconstruction) allows for the use of individualized data processing, including filters, suited to the source data, thereby focusing on specific aspects of the source data, including, for example, noise and artifact reduction, resolution, edge preservation, etc. Combining the separately processed data results in an optimized balance of these aspects with improved image quality.

20 Claims, 16 Drawing Sheets

(51) Int. Cl.
*A61N 5/10* (2006.01)
*A61B 6/03* (2006.01)

(52) U.S. Cl.
CPC ............ *A61B 6/4291* (2013.01); *A61B 6/466* (2013.01); *A61N 5/1031* (2013.01); *A61N 5/1081* (2013.01)

(58) Field of Classification Search
CPC ......... G01N 23/20083; G01N 23/2206; G16H 50/50; G01T 1/161; G01T 1/1647; G01T 1/2018; G01T 1/22; G01T 1/1641; G01T 1/1642; G01T 1/1648; G01T 1/295; G01T 7/00; G01T 1/249; G01T 1/2985; H01J 2237/31791; H01J 37/3174; A61B 6/5282; A61B 6/032; A61B 6/4291; A61B 6/482; A61B 6/502; A61B 6/583; A61B 5/4312; A61B 5/7257; A61B 6/4035; A61B 5/05; A61B 5/0507; A61B 6/06; A61B 8/0825; A61B 6/4041; A61B 6/405; A61B 6/483; A61B 8/14; A61B 8/15; A61B 8/406; A61B 8/4209; A61B 6/4085; A61B 6/0492; A61B 6/445; A61B 6/4233; A61B 6/466; A61B 6/5205; A61B 6/5258; A61B 2090/3908; A61B 2090/3937; A61B 2090/3966; A61B 5/1075; A61B 6/025; A61B 6/0414; A61B 6/4417; A61B 6/461; A61B 6/5217; A61B 6/037; A61B 6/5235; A61B 2034/102; A61B 2034/104; A61B 2034/105; A61B 34/10; A61B 6/035; A61B 6/4021; A61B 6/4441; A61B 5/055; A61B 6/027; A61B 6/0407; A61B 6/0487; A61B 6/08; A61B 6/4014; A61B 6/0428; A61B 6/4064; A61B 6/4078; G06T 11/005; G06T 11/003; G06T 7/60; G06T 11/20; G06T 2207/10081; G06T 2207/30004; G06T 2211/424; G06T 5/00; G06T 5/002; G06T 7/0012; G06T 11/006; G06T 2207/10112; G06T 2207/30068; G06T 11/008; G06T 2210/41; G06T 2200/04; G06T 2207/10072; G06T 2207/20128; G06T 2207/20224; G06T 5/003; G21K 1/10; G21K 5/04; G21K 1/02; G21K 1/025; A61N 2005/1061; A61N 5/1067; A61N 2008/1085; A61N 2005/1091; A61N 2005/1095; A61N 5/1042; A61N 5/1049; A61N 5/107; A61N 5/1071; A61N 5/1081; A61N 5/1082; A61N 5/103
USPC ............... 378/4, 7, 8, 19, 62, 65, 70, 86, 87
See application file for complete search history.

(56) References Cited

U.S. PATENT DOCUMENTS

| | | | | |
|---|---|---|---|---|
| 5,903,008 | A * | 5/1999 | Li | ............... G01T 1/1647 250/363.04 |
| 6,233,478 | B1 | 5/2001 | Liu | |
| 6,307,909 | B1 | 10/2001 | Flohr et al. | |
| 7,050,528 | B2 | 5/2006 | Chen | |
| 7,336,759 | B2 | 2/2008 | Nukui | |
| 7,636,415 | B2 * | 12/2009 | Popescu | .............. A61B 6/032 378/7 |
| 7,660,380 | B2 | 2/2010 | Boese et al. | |
| 7,760,855 | B2 * | 7/2010 | Ruhrnschopf | ......... A61B 6/482 378/87 |
| 7,957,502 | B2 * | 6/2011 | Manabe | ............... G06T 11/005 378/7 |
| 8,467,497 | B2 | 6/2013 | Lu et al. | |
| 8,744,161 | B2 * | 6/2014 | Flohr | ............... A61B 6/4014 382/131 |
| 8,818,065 | B2 * | 8/2014 | Yang | ............... A61B 6/5282 382/131 |
| 8,873,703 | B2 * | 10/2014 | Ruimi | ............... G01T 1/2985 378/7 |
| 9,285,326 | B2 * | 3/2016 | Gagnon | ............ A61B 6/4291 |
| 9,320,477 | B2 * | 4/2016 | Liu | ............... A61B 6/032 |
| 2003/0076927 | A1 | 4/2003 | Nakashima et al. | |
| 2004/0091079 | A1 | 5/2004 | Zapalac | |
| 2004/0202360 | A1 | 10/2004 | Besson | |
| 2005/0053188 | A1 | 3/2005 | Gohno | |
| 2006/0262894 | A1 | 11/2006 | Bernhardt et al. | |
| 2007/0127621 | A1 | 6/2007 | Grass et al. | |
| 2007/0189444 | A1 | 8/2007 | Van Steven-Daal et al. | |
| 2008/0103834 | A1 | 5/2008 | Reiner | |
| 2008/0112532 | A1 | 5/2008 | Schlomka | |
| 2009/0080603 | A1 | 3/2009 | Shukla et al. | |
| 2009/0161826 | A1 | 6/2009 | Gertner et al. | |
| 2009/0225932 | A1 | 9/2009 | Zhu et al. | |
| 2009/0304142 | A1 | 12/2009 | Ruimi et al. | |
| 2010/0046819 | A1 | 2/2010 | Noo et al. | |
| 2011/0255656 | A1 | 10/2011 | Star-Lack et al. | |
| 2012/0207370 | A1 | 8/2012 | Fahimian et al. | |
| 2012/0263360 | A1 | 10/2012 | Zhu et al. | |
| 2012/0294504 | A1 | 11/2012 | Kyriakou | |
| 2014/0018671 | A1 | 1/2014 | Li et al. | |
| 2014/0169652 | A1 | 6/2014 | Vic et al. | |
| 2016/0220844 | A1 | 8/2016 | Paysan et al. | |
| 2017/0205360 | A1 | 7/2017 | Cinquin et al. | |
| 2017/0332982 | A1 | 11/2017 | Koehler et al. | |
| 2018/0345042 | A1 | 12/2018 | Voronenko et al. | |
| 2019/0099149 | A1 | 4/2019 | Li | |
| 2020/0016432 | A1 | 1/2020 | Maolinbay | |
| 2020/0121267 | A1 | 4/2020 | Deutschmann | |
| 2020/0402644 | A1 | 12/2020 | Zhou et al. | |

FOREIGN PATENT DOCUMENTS

| | | | |
|---|---|---|---|
| JP | 2004136021 A | | 5/2004 |
| WO | 2006078386 A2 | | 7/2006 |

OTHER PUBLICATIONS

Defrise, et al., A solution to the long-object problem in helical cone-beam tomography, Physics in Medicine and Biology, 2000, pp. 623-643, vol. 45.

Hsieh, et al., A novel reconstruction algorithm to extend the CT scan field-of-view, Med. Phys., Sep. 2004, pp. 2385-2391, vol. 31, No. 9.

International Search Report and Written Opinion from PCT/US2019/063073 dated Apr. 3, 2020.

International Search Report and Written Opinion from PCT/US2019/063076 dated Mar. 16, 2020.

International Search Report and Written Opinion from PCT/US2019/063077 dated Mar. 16, 2020.

International Search Report and Written Opinion from PCT/US2019/063078 dated Oct. 8, 2020.

International Search Report and Written Opinion from PCT/US2019/063080 dated Mar. 16, 2020.

International Search Report and Written Opinion from PCT/US2019/063085 dated Mar. 16, 2020.

International Search Report and Written Opinion from PCT/US2019/063087 dated Apr. 3, 2020.

Kang et al., Accurate positioning for head and neck cancer patients using 2D and 3D image guidance, Journal of Applied Clinical Medical Physics, Mar. 2011, pp. 1-14, vol. 12, No. 1.

Katsevich, A., An improved exact filtered backprojection algorithm for spiral computed tomography, Advances in Applied Mathematics, 2004, pp. 691-697, vol. 32.

Maslowski, et al., Acuros CTS: A fast, linear Boltzmann transport equation solver for computed tomography scatter—Part I: Core algorithms and validation, Med. Phys., 2018, pp. 1-15.

(56) References Cited

OTHER PUBLICATIONS

Ning, et al., X-ray scatter correction algorithm for cone beam CT imaging, Med. Phys., May 2004, pp. 1195-1202, vol. 31, No. 5.

Office Action from U.S. Appl. No. 16/694,202 dated Apr. 9, 2021, 12 pages.

Office Action from U.S. Appl. No. 16/694,218 dated Apr. 15, 2021, 7 pages.

Office Action from U.S. Appl. No. 16/694,230 dated Apr. 1, 2021, 6 pages.

Ramamurthi et al., Region of Interest Cone Beam Tomography With Prior CT Data, Conference Record of the 37th Asilomar Conference on Signals, Systems, & Computers, Nov. 2003, pp. 1924-1927, vol. 2.

Siewerdsen, et al., A simple, direct method for x-ray scatter estimation and correction in digital radiography and cone-beam CT, Med. Phys., Jan. 2006, pp. 187-197, vol. 33, No. 1.

Spearman, et al., Effect of Automated Attenuation-based Tube Voltage Selection on Radiation Dose at CT: An Observational Study on a Global Scale, Radiology, Apr. 2016, pp. 167-174, vol. 279, No. 1.

Sun, et al., Improved scatter correction using adaptive scatter kernel superposition, Physics in Medicine and Biology, Oct. 2010, pp. 6695-6720, vol. 55.

Tang, et al., A sinogram extrapolation method for CT field of view extension, Proceedings of the Fifth CT Meeting, 2018, pp. 206-209.

Yu, et al.. Radiation dose reduction in computed tomography: techniques and future perspective, Imaging Med., Oct. 2009, pp. 65-84, vol. 1.

Zbijewski, et al.. Efficient Monte Carlo Based Scatter Artifact Reduction in Cone-Beam Micro-CT, IEEE Transactions on Medical Imaging, Jul. 2006, pp. 817-827, vol. 25, No. 7.

Zhu, et al. Noise suppression in scatter correction for cone-beam CT, American Association of Physicists in Medicine, 2009, pp. 741-752, vol. 36, No. 3.

Zhu, et al.. Scatter Correction Method for X-ray CT Using Primary Modulation: Theory and Preliminary Results, IEEE Transactions on Medical Imaging, Dec. 2006, pp. 1573-1587, vol. 25, No. 12.

Office Action from U.S. Appl. No. 16/694,161 dated Sep. 13, 2021, 18 pages.

\* cited by examiner

NOISE AND ARTIFACT REDUCTION FOR IMAGE SCATTER CORRECTION

CROSS-REFERENCE TO RELATED APPLICATIONS

This application is related to U.S. patent application Ser. No. 16/694,145, entitled "MULTIMODAL RADIATION APPARATUS AND METHODS," filed Nov. 25, 2019, and U.S. patent application Ser. No. 16/694,148, entitled "APPARATUS AND METHODS FOR SCALABLE FIELD OF VIEW IMAGING USING A MULTI-SOURCE SYSTEM," filed Nov. 25, 2019, both of which are incorporated by reference herein in their entirety.

FIELD OF THE INVENTION

Aspects of the disclosed technology relate to improving quality during radiological image processing, including, for example, reducing noise and artifacts associated with scatter and scatter correction, and, more particularly, to processing a scatter-corrected image as a non-scatter-corrected component and a scatter-only component.

BACKGROUND

Tomography is a noninvasive, radiological imaging technique that is used to generate cross-sectional images of a three dimensional (3D) object without superimposing tissues. Tomography can be categorized into transmission tomography, such as computed tomography (CT) and emission tomography like single photon emission computed tomography (SPECT) and positron emission tomography (PET). CT is a technique based on x-ray transmission through a patient to create images of sections of the body. Photon emission computed tomography and positron emission tomography provide 3D image information about the radionuclide injected into the patient that shows the metabolic and physiological activities within an organ.

In tomographic scans, projections are acquired from many different angles around the body by one or more rotating detectors (along with rotating radiation sources in CT). These data are then reconstructed to form 3D images of the body. For example, the reconstruction of tomographic images can be achieved via filtered backprojection and iterative methods.

The quality of the final image is limited by several factors. Some of these are the attenuation and scatter of gamma ray photons, the detection efficiency, the spatial resolution of the collimator-detector system, etc. These factors can cause poor spatial resolution, low contrast, and/or high noise levels. Image data processing (e.g., filtering) techniques can be used to improve the quality of the image.

In CT, including cone-beam CT, the primary signal detected by a detector element represents the x-rays that come out from the tube, penetrate the patient body, and reach or are detected by the detector. The x-rays in the primary signal travel along the x-ray paths that connect the tube focal point of the tube to the detecting detector elements. The scatter signal detected by the same element also represents the x-rays that are scattered into the elements. The primary signal allows the reconstruction of CT images. The scatter signal, however, can degrade the CT images, both quantitatively and qualitatively.

Scatter in various radiological imaging modalities, including CT and cone-beam CT, can account for a significant portion of the detected photons. Scatter can negatively impact image quality, including contrast and quantitative accuracy. Consequently, scatter measurement, estimation, and correction are applicable to data processing and image reconstruction, including in the context of image-guided radiation treatment (IGRT). IGRT can make use of medical imaging technology, such as CT, to collect images of a patient before, during, and/or after treatment.

Software-based scatter correction in various radiological imaging modalities can significantly increase the noise as compared to without scatter correction. For example, in the case of low count scans (low applied dose and/or large patients), significant scatter noise associated with scatter correction at certain angles may be amplified and appear as strong streak artifacts in the reconstructed image. Noise reduction for scatter correction is hence a challenging task for image generation.

BRIEF SUMMARY

In one embodiment, a method of generating a radiological image includes receiving radiation data from a radiological imaging apparatus, wherein the radiation data comprises a primary component and a scatter component, generating a non-scatter-corrected data set based on the radiation data and using a first data processing technique, estimating the scatter component of the radiation data, generating a scatter-only data set based on the scatter estimate and using a second data processing technique, wherein the second data processing technique is different than the first data processing technique, and generating an image based on the non-scatter-corrected data set and the scatter-only data set.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
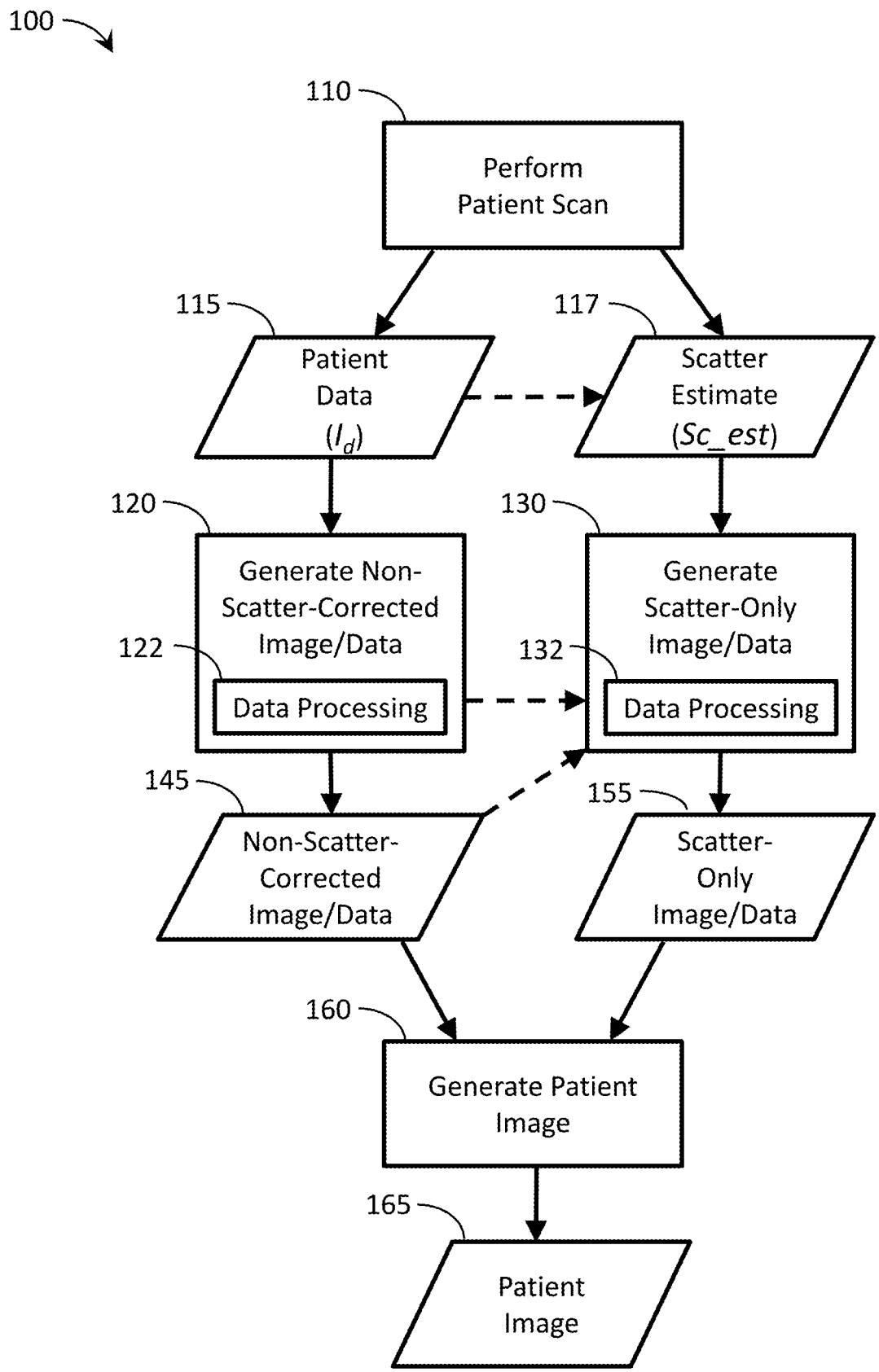
FIG. 1 a flow chart depicting an exemplary method of generating a radiological image by treating the imaging data as a non-scatter-corrected component and a scatter-only component.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), field-programmable gate arrays (FPGAs), graphics processing units (GPUs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

In a CT scan, the x-ray reference data ($I_0$) that is the signal when there is no patient (and patient table). When the raw or patient data ($I_d$) is acquired, the ratio of the flux to the signal at each detector element is computed. The log of the ratio is the line integral of the linear attenuation of the patient along the corresponding x-ray path if the patient data has only the primary signal (Pr). Subsequently, CT images can be reconstructed from the line integrals measured by all the detector elements in many angles around the patient.

Since the detected signal includes both the primary (Pr) and scatter signal (Sc), where $I_d$=Pr+Sc, the direct calculation of the ratio of the reference to the detector signal, $I_0/I_d$, is no longer the integral of the linear attenuation of the patient along the x-ray path (l) since it is contaminated by the scatter component (Sc) in the signal. Explicitly, the correct line integral should be l=log($I_0$/Pr). But with scatter, the calculated ration is shown in equation 1:

$$ld = \log(I_0/I_d), \quad (1)$$

where $I_d$=Pr+Sc.

Sine the scatter (Sc) is a positive value, without scatter correction, the calculated line integral will be less than the true line integral (without (Sc)). Reconstruction using the contaminated line integral ld will lead to quantitative bias in the image, and qualitatively, reduce contrast and introduce artifacts to the images.

In order to handle the scatter issue above, clinical CT systems can use hardware approaches to minimize scatter during data acquisition upfront and once data is acquired, as well as apply software approaches to correct the residual scatter in the measured data. The latter can be referred to as scatter correction.

The principle of scatter correction is to estimate the scatter (Sc_est) and remove or subtract the estimated scatter from the patient data and calculate the corrected line integral according to equation 2:

$$l_{corr} = \log\left(\frac{I_0}{I_d - \text{Sc\_est}}\right) = \log\left(\frac{I_0}{Pr + (Sc - \text{Sc\_est})}\right) \quad (2)$$

If the approach is accurate so that the scatter estimate (Sc_est) is the same as the scatter component in the measured data, then equation 2 leads to the correct line integral that will allow an accurate CT image reconstruction.

From an image noise point of view, however, scatter correction increases the noise in the calculated line integral, leading to increased noise in the reconstructed image. The variance (noise) of the line integral without scatter correction is shown in equation 3:

$$\text{Var\_Id} = \left(\frac{1}{Id}\right)^2 \times \text{Var\_Id}, \quad (3)$$

where Var_Id is the variance of the measured patient data Id, assuming variance of $I_0$ is 0.

The variance of the line integral after scatter correction is shown in equation 4:

$$\text{Var\_corr} = \left(\frac{1}{I_d - \text{Sc\_est}}\right)^2 \text{Var\_Id} + \left(\frac{1}{I_d - \text{Sc\_est}}\right)^2 \text{Var\_Sc\_est}, \quad (4)$$

where Var_Sc_est is the variance (noise) of the estimated scatter (Sc_est) (assuming the noise of the estimated scatter is independent from the noise of the measure data).

Comparing the noise of the scatter corrected line integral in equation 4 and that of the non-scatter corrected line integral in equation 3, shows that, even if the scatter estimate (Sc_est) has no noise, the noise of the calculated line integral is amplified by a factor shown in equation 5:

$$\left(\frac{I_d}{I_d - \text{Sc\_est}}\right)^2. \quad (5)$$

The noise amplification in equation 5 increases when the percentage of scatter in the measured data increases. For example, if 50% of the measured data is scatter, then the noise is amplified by a factor of 4. In cone-beam CT systems that use anti-scatter grids, where the residual scatter can be 30% of the data, equation 5 predicts a noise amplification of about a factor of 2 with scatter correction as compared to without scatter correction. In cone-beam CT with flat-panel detectors where no anti-scatter grid is deployed, scatter can be more than 50% of the total measured data, and the larger the patient, the more the scatter.

Use of conventional noise reduction approaches for scatter correction could: (a) reduce the noise of the estimated scatter, which corresponds to reducing the noise in the second term in the right-hand-side of equation 4; (b) reduce noise in the scatter corrected raw data or line integral; (c) model scatter in an iterative reconstruction as an additive term to the estimated primary and compare the sum of the estimated primary and scatter to the measured data; (d) regularize noise in reconstruction; or (e) filter/denoise the scatter corrected image.

While all these approaches may have benefits in certain situations and to certain degrees, the drawbacks are many. For approach (a), even if one could make the scatter perfect with no noise, the noise is still amplified by the factor shown in equation 5 and can be very significant in CT scans with a significant amount of scatter, especially for cone-beam CT with a large imaging field-of-view and without anti-scatter grids. The approach in (b) not only carries the drawback of (a), but also may lose signal (resolution and contrast), since the raw data is filtered due to noise reduction. The approach in (c) not only requires a more sophisticated reconstruction algorithm and a much longer reconstruction time, but also the noise reduction is limited. Approaches in (d) are challenged by how the regularization is designed. The challenge can be easily understood if one considers the scatter corrected image as a combination of non-scatter corrected component and the scatter correction component. The non-scatter corrected component is of much lower noise than the scatter correction component. Therefore, when the regularization is applied to the entire image to optimize the noise reduction for the high-noise scatter component, it tends to over-regularize the low-noise non-scatter corrected component of the image. Post reconstruction image processing (filtering)/denoise in (e) shares the same challenge as (d) in not being able to optimize the two components that are of very different noise level.

In embodiments disclosed herein, the scatter corrected image can be treated as the combination of two components: one is the non-scatter corrected component and the other is the scatter only component. The line integral in equation 2 is rewritten as the sum of two components as shown in equation 6:

$$l_{corr} = \log\left(\frac{I_0}{I_d}\right) + \left[\log\left(\frac{I_0}{I_d - \text{Sc\_est}}\right) - \log\left(\frac{I_0}{I_d}\right)\right]. \quad (6)$$

The first term in the right-hand-side of equation 6 is the line integral without scatter correction. The term in the square brackets is the scatter correction component of the line integral. For analytical reconstruction, the reconstruction of the corrected line integral is equivalent to the reconstruction of the two terms separately to generate two images, followed by the summation of the two images to obtain the final scatter corrected image. The image reconstructed from the first term is equivalent to the conventional non-scatter corrected image (noSC image). The image reconstructed from the second term can be referred to as the scatter-only image (Scatter-only image). Explicitly, shown in equation 7:

$$\text{CT image} = \text{noSC image} + \text{Scatter-only image} \quad (7)$$

In this manner, the scatter estimate (Sc_est) can be removed from the patient data. From the analysis above, it is clear that the Scatter-only image carries the scatter correction related noise and artifacts. The noSC image is of much lower noise than the Scatter-only image, and the overall CT image is the combination of the two.

Conventional noise reduction associated with scatter correction, whether in the raw data or post reconstruction image, or in the reconstruction process, is essentially operating on the combined noSC and Scatter-only components of the data/image, even though the two components have very different noise levels. An approach that optimally suppresses the noise in the Scatter-only component may lead to over smoothing (hence resolution degradation) of the noSC component; and an approach that minimizes resolution degradation may not be effective to suppress the noise associated with scatter correction.

The embodiments described herein achieve improved image quality after scatter correction, including, for example, both sufficient noise reduction and minimal resolution degradation. In these embodiments, treating the Scatter-only image separately from and differently than the noSC image can reduce noise and artifacts associated with scatter and scatter correction. Due to the much higher noise in the Scatter-only image, a stronger noise suppression data processing technique (e.g., filter) can be applied to the Scatter-only image to optimize noise reduction. Yet, a lighter noise suppression data processing technique (e.g., filter) can be applied to the noSC image to minimize the resolution loss. Therefore, the two image components in equation 7 are optimized independently, and the combined final image (e.g., CT image) can have an optimized compromise of noise reduction and resolution preservation.

In some embodiments, using the noSC image to guide the noise reduction of the high noise Scatter-only image can have further benefits. Since the noSC image has much lower noise level than the Scatter-only image, it can be used to guide the noise reduction of the Scatter-only image. For example, "guiding" can include determining the filter kernel and any associated parameters. This guided noise reduction of the Scatter-only image can lead to Scatter-only images with noise similar to or even lower than the noSC image. The edges in the noSC images can provide reliable edge-preserving guidance of the data processing (e.g., filtering) of the Scatter-only image. Therefore, the combined final image (e.g., CT image) can have a noise level similar to that in the noSC image, while edge-preservation is optimized.

In various embodiments, reconstructing the two components in the right-hand-side of equation 6 differently, for example, using a higher resolution filter (kernel) to reconstruct the noSC component and a more smoothing filter (lower resolution kernel) to reconstruct the Scatter-only component.

The following flow charts and block diagrams illustrate exemplary configurations and methodologies associated with scatter correction and/or image generation. The exemplary methodologies may be carried out in logic, software, hardware, or combinations thereof. In addition, although the procedures and methods are presented in an order, the blocks may be performed in different orders, including series and/or parallel. Thus, the steps below, including imaging, image-based pre-delivery steps, and treatment delivery, although shown sequentially, may be executed simultaneously, including in real-time. Further, additional steps or fewer steps may be used.

FIG. 1 is a flow chart depicting an exemplary method 100 of generating a radiological image by treating (processing, e.g., via a data processing technique, algorithm, filter, etc.) the imaging data as a non-scatter-corrected component and a scatter-only component. In this manner, the data processing technique applied to the non-scatter-corrected component and the scatter-only component is separate and distinct, as opposed to a data processing technique being applied to the combined data. In this embodiment, a patient scan is performed at step 110, generating radiation/patient data ($I_d$) 115. A scatter estimate (Sc_est) 117 is also generated. The scatter estimate 117 can be generated in any suitable manner, including based on the patient data 115, scatter-only measurements, and/or information associated with the scanning apparatus, including, for example scan models, parameters, settings, etc. In various embodiments, scatter-only measurements may be from active portions of the radiation detector blocked from direct radiation (primary data), for example, by a beam former or collimator.

In this manner, the method then proceeds to treat the imaging data as a combination of the two components detailed above (as shown in equation 7): 1) the non-scatter corrected component; and 2) the scatter only component.

At step 120, the method generates at least one non-scatter-corrected data set 145 (e.g., line integral, image, and/or other data) based on the patient data 115 and using data processing technique 122, which may include, for example, a filter. At step 130, the method generates at least one scatter-only data set 155 (e.g., line integral, image, and/or other data) based on the scatter estimate 117 and using data processing technique 132, which may include, for example, another filter. In various embodiments, and as discussed below in other embodiments, one or more various types of data processing techniques may be utilized during steps 120, 130, including during different steps or sub-steps of image data processing.

Data processing techniques or steps, as described herein, include software-based, mathematical processing of imaging data (e.g., an operation applied to data associated with pixels/voxels of image data). Primary goals of applying data processing techniques to imaging data can include suppressing noise, preserving spatial resolution and contrast, smoothing, reduce artifacts, and edge enhancement.

For example, in various embodiments, data processing techniques or steps can include applying one or more filters to the data. In image processing, these filters can include, for example, a kernel, convolution matrix, mask, etc. These filters can be used for blurring, sharpening, embossing, edge detection, etc. For example, in several embodiments, this is accomplished by doing a convolution between a kernel and an image. Data processing, including via filters, can be applied to the imaging data before, during, and/or after reconstruction. For example, in one embodiment, radiation/patient data ($I_d$) 115 comprises raw x-ray data, which are the values of all measured detector signals during a CT scan. After calibration, for example, for fluctuations in tube output and beam hardening, the attenuation properties of each x-ray signal are accounted and correlated with the ray position. From these data, the CT images are reconstructed, including the use of mathematical procedures like convolution filtering and back-projection. A convolution filter is a mathematical filter function (a kernel) applied during image reconstruction of CT imaging data. Reconstruction filters can include sin c filters (e.g., windowing (e.g., Lanczos, Kaiser), spline, etc.), Gaussian, B-splines (e.g., box filter, tent filter), etc. In addition to reconstruction, other filters can be used for resampling, interpolation, anti-aliasing, etc.

Various types of data processing techniques, including via filters, for example, can be used to smooth or to enhance edges, can be selected according to the type of source data (e.g., primary data, primary and scatter data, scatter-only data, etc.), application (CT, CBCT, PET, SPECT, etc.), desired computational speed, tissue characteristics, etc. Other types of data processing techniques can include, for example, noise reduction through wavelet transformation, singular value decomposition, etc. For example, for singular value decomposition, different eigenvalues can be used for the scatter only component and the non-scatter component. References to filters in the embodiments below are exemplary; other types of data processing techniques may also be used in place of or in addition to the filter.

In various embodiments, data processing technique 132 is different than data processing technique 122, where the data processing techniques (e.g., filters) 122, 132 and their associated parameters are specifically directed to the associated data 115, 117. In this manner, the data processing techniques 122, 132 can be separately optimized for the source data 115, 117. For example, utilization of different data processing techniques 122, 132 during processing of separate data 115, 117, respectively, can achieve both sufficient noise reduction and minimal resolution degradation. In these embodiments, processing the scatter estimate 117 (Scatter-only) separately from and differently than the patient data 115 (noSC) can improve quality (e.g., reduce noise and artifacts associated with scatter and scatter correction), as discussed above. In particular, for example, due to higher noise in the scatter estimate 117, a data processing technique (e.g., filter) 132 with stronger noise suppression (e.g., smoothing kernel) can be applied to the scatter-only image data to optimize noise reduction. In contrast, a data processing technique (e.g., filter) 122 with lighter noise suppression (e.g., high-resolution kernel) can be applied to the non-scatter-corrected image data to minimize the resolution loss. In this manner, the two imaging data components (non-scatter-corrected and scatter only, as shown in equation 7) are processed (optimized) independently.

In some embodiments, the non-scatter-corrected image/data, before or after processing by data processing technique (e.g., filter) 122, can be used to guide the processing by data processing technique (e.g., filter) 132 (e.g., to determine the filter kernel for noise reduction) of the relatively high noise scatter-only image/data. As discussed above, since the non-scatter corrected image/data has much lower noise level than the scatter-only image/data, it can be used to guide the noise reduction of the scatter-only image/data at step 130.

At step 160, the method generates a patient image 165 based on the non-scatter-corrected data set 145 and the scatter-only data set 155 (e.g., by removing the scatter from the patient data). For example, in an embodiment where the data sets are line-integral components, the scatter-only data set 155 can be added to the non-scatter-corrected data set 145 to yield the patient image 165. In one exemplary embodiment, based on the independent processing at steps 120, 130 with the respective data processing techniques (e.g., filters) 122, 132 described above, the combined final image 165 (e.g., CT image) can have an optimized compromise of noise reduction and resolution preservation.

The method 100 is applicable to embodiments processing imaging data before or after reconstruction (i.e., in the data or volume/image domain), including those detailed in the embodiments below. References to the optional filters in the embodiments below are used as exemplary data processing. Other types of data processing techniques may be used without, in place of, or in addition to the exemplary filters mentioned.

Figure 2:
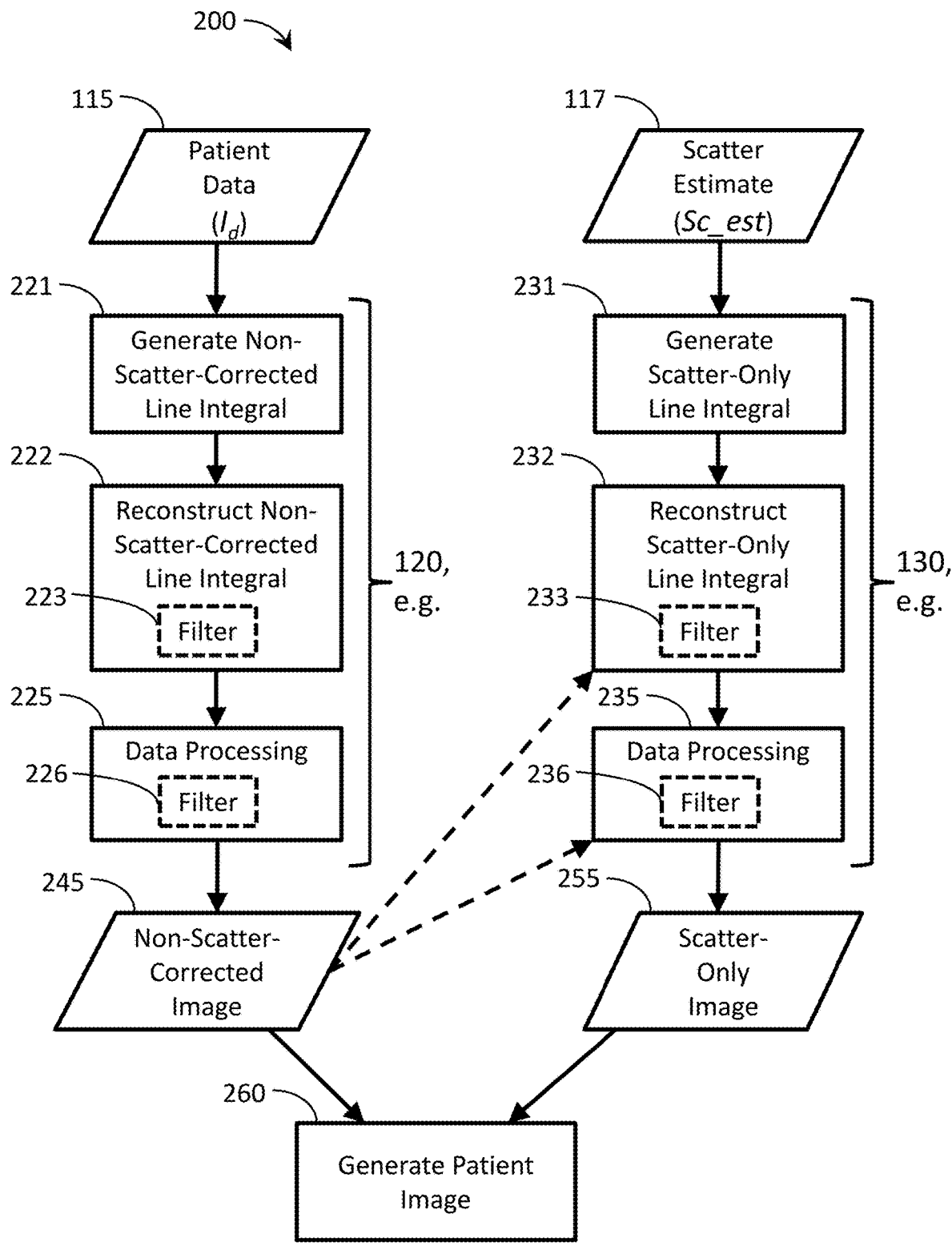
FIG. 2 is a flow chart depicting another exemplary method of generating a radiological image by treating the imaging data as a non-scatter-corrected component and a scatter-only component.

FIG. 2 is a flow chart depicting another exemplary method 200 of generating a radiological image by treating the imaging data as a non-scatter-corrected component and a scatter-only component. In this embodiment, radiation/patient data ($I_d$) 115 and scatter estimate (Sc_est) 117 may be generated as described in method 100, including via a patient scan 110.

At step 221, the method generates at least one non-scatter-corrected line integral based on the patient data 115. Next, the non-scatter-corrected line integral is reconstructed at step 222 and processed at step 225 to generate a non-scatter-corrected image 245. These steps 222, 225 may be performed together or in any order. For example, in this and other embodiments mentioned below, reconstruction and data processing can be combined (e.g., where reconstruction of the data can include the data processing), can include one or more of each step, and/or can include one or more data processing techniques. In one embodiment, if steps 222, 225 are performed separately (as depicted in FIG. 2), then each step may utilize an associated filter 223, 226. In another embodiment, if steps 222, 225 are performed together, then only one filter 223 may be utilized. As mentioned above, processing may be performed before, during, and/or after reconstruction in various embodiments. In one embodiment, steps 221, 222, 225 may be associated with an exemplary implementation of step 120.

At step 231, the method generates at least one scatter-only line integral based on the scatter estimate 117. Next, the scatter-only line integral is reconstructed at step 232 and processed at step 235 to generate a scatter-only image 255. These steps 232, 235 may be performed together or in any order. In one embodiment, if steps 232, 235 are performed separately (as depicted in FIG. 2), then each step may utilize an associated filter 233, 236. In another embodiment, if steps 232, 235 are performed together, then only one filter 233 may be utilized. As mentioned above, processing may be performed before, during, and/or after reconstruction in various embodiments. In one embodiment, steps 231, 232, 235 may be associated with an exemplary implementation of step 130.

As discussed above, in various embodiments, one or more filters 233 236 is different than one or more filters 223, 226, where the filters and their associated parameters can be specifically directed to the associated data 115, 117. As discussed above in detail, the filters can be separately optimized for the source data 115, 117, independently optimizing the processing (filtering) of the two imaging data components (non-scatter-corrected and scatter only, as shown in equation 7).

In some embodiments, the non-scatter-corrected image 245, before or after processing, can be used to guide the processing, for example, with filter 233 and/or filter 236 (i.e., to determine the filter kernel, e.g., for noise reduction), of the relatively high noise scatter-only image/data. For example, in one embodiment, data processing of the scatter-only data can include application of a Gaussian filter that uses a voxel difference in the non-scatter-corrected image 245 to determine kernel weights for the Gaussian filter. When designing a filter for the scatter-only data, the non-scatter corrected image 245, which has lower noise, can be used to determine (guide) the kernels of a filter (e.g., filter 233 or filter 236) to be used to filter the scatter-only data to generate the scatter-only image 255. In one embodiment, this can be achieved by decreasing the kernel weight for pixels on an edge (in the non-scatter corrected image) and to increase the weight, or increase the kernel size for an area with no edge (in the non-scatter corrected image), and then use the kernel to filter the scatter-only data. As discussed above, since the non-scatter corrected image/data has much lower noise level than the scatter-only image/data, it can be used to guide the noise reduction of the scatter-only image/data.

At step 260, the method generates a patient image based on the non-scatter-corrected image 245 and the scatter-only image 255. For example, the scatter-only image 255 can be added to the non-scatter-corrected image 245 to yield the patient image, for example, according to equation 7.

Figure 3:
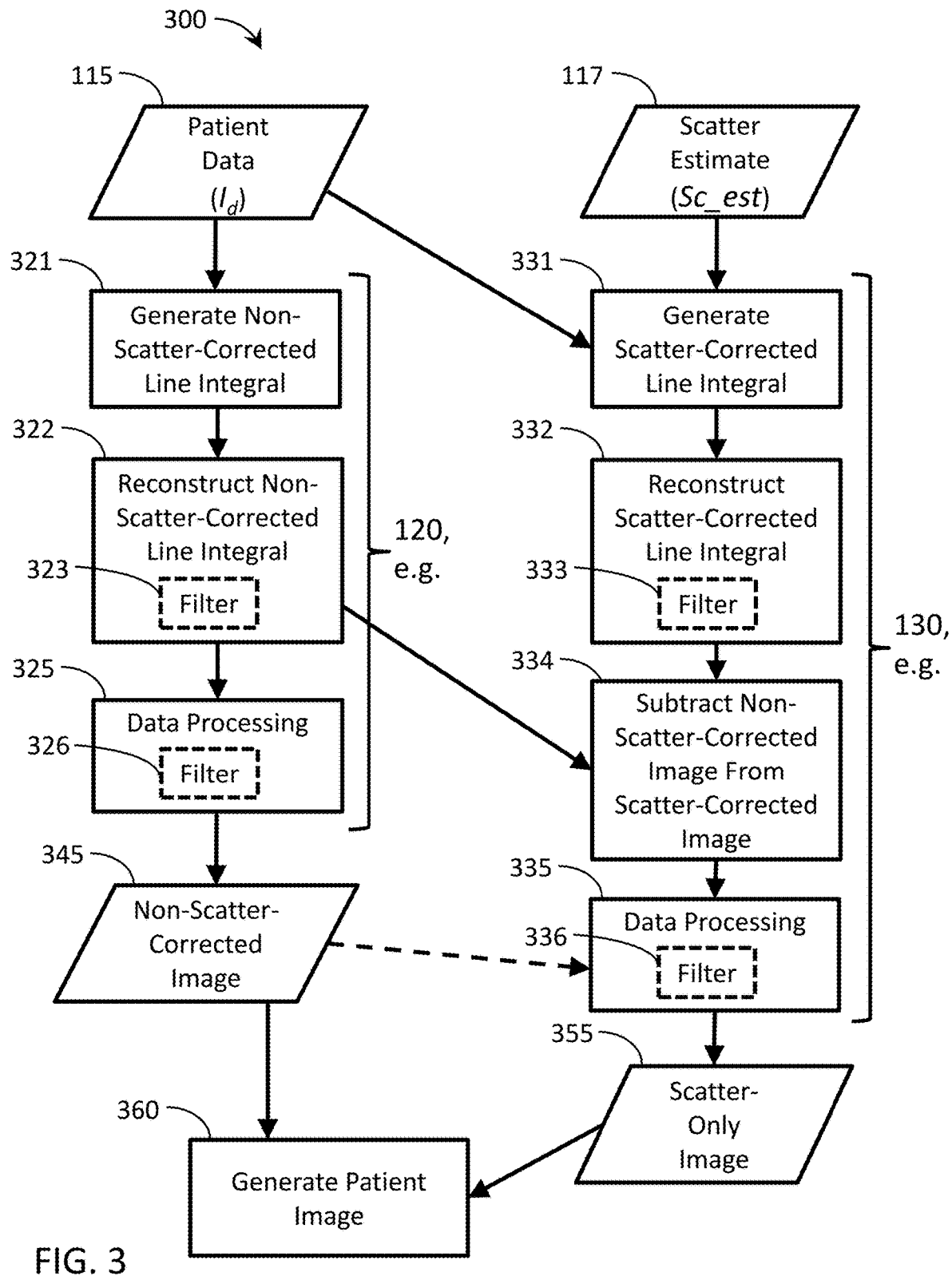
FIG. 3 is a flow chart depicting another exemplary method of generating a radiological image by treating the imaging data as a non-scatter-corrected component and a scatter-only component.

FIG. 3 is a flow chart depicting another exemplary method 300 of generating a radiological image by treating the imaging data as a non-scatter-corrected component and a scatter-only component. In this embodiment, radiation/patient data ($I_d$) 115 and scatter estimate (Sc_est) 117 may be generated as described in method 100, including via a patient scan 110.

At step 321, the method generates at least one non-scatter-corrected line integral based on the patient data 115. Next, the non-scatter-corrected line integral is reconstructed at step 322 and processed at step 325 to generate a non-scatter-corrected image 345. These steps 322, 325 may be performed together or in any order. In one embodiment, if steps 322, 325 are performed separately (as depicted in FIG. 3), then each step may utilize an associated filter 323, 326. In another embodiment, if steps 322, 325 are performed together, then only one filter 323 may be utilized. As mentioned above, processing may be performed before, during, and/or after reconstruction in various embodiments. In one embodiment, steps 321, 322, 325 may be associated with an exemplary implementation of step 120.

At step 331, the method generates at least one scatter-corrected line integral based on the patient data 115 and the scatter estimate 117. Next, the scatter-corrected line integral is reconstructed at step 332. A filter 333 may be utilized before, during, or after reconstruction. Then, at step 334, the method determines a difference between the reconstructed non-scatter-corrected line integral from step 322 and the reconstructed scatter-corrected line integral from step 332. For example, in one embodiment, —the non-scatter-corrected image is subtracted from the scatter-corrected image to yield scatter-only image data. Then, at step 335, the difference can be processed using filter 336 to generate a scatter-only image 355. In one embodiment, steps 331, 332, 334, 335 may be associated with an exemplary implementation of step 130.

As discussed above, in various embodiments, one or more filters 333 336 is different than one or more filters 323, 326, where the filters and their associated parameters can be specifically directed to the associated data 115, 117. As discussed above in detail, the filters can be separately optimized for the source data 115, 117, independently optimizing the processing (filtering) of the two imaging data components (non-scatter-corrected and scatter only, as shown in equation 7).

In some embodiments, the non-scatter-corrected image 345, before or after processing, can be used to guide the processing, for example, with filter 336 (i.e., to determine the filter kernel, e.g., for noise reduction), of the relatively high noise scatter-only image/data. As discussed above, since the non-scatter corrected image/data has much lower noise level than the scatter-only image/data, it can be used to guide the noise reduction of the scatter-only image at step 335.

At step 360, the method generates a patient image based on the non-scatter-corrected image 345 and the scatter-only image 355. For example, the scatter-only image 355 can be added to the non-scatter-corrected image 345 to yield the patient image.

Figure 4:
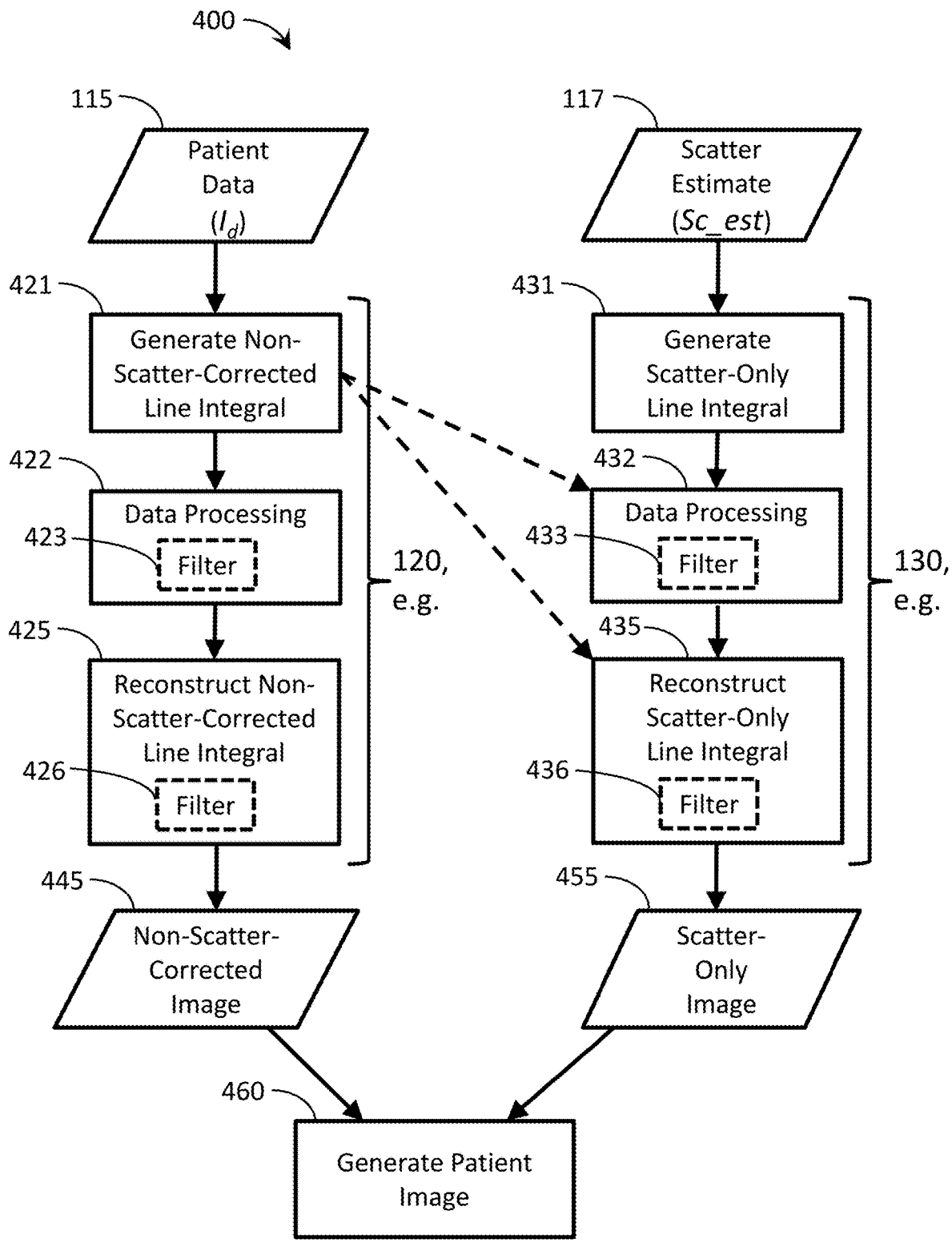
FIG. 4 is a flow chart depicting another exemplary method of generating a radiological image by treating the imaging data as a non-scatter-corrected component and a scatter-only component.

FIG. 4 is a flow chart depicting another exemplary method 400 of generating a radiological image by treating the imaging data as a non-scatter-corrected component and a scatter-only component. In this embodiment, radiation/patient data ($I_d$) 115 and scatter estimate (Sc_est) 117 may be generated as described in method 100, including via a patient scan 110.

At step 421, the method generates at least one non-scatter-corrected line integral based on the patient data 115. Next, the non-scatter-corrected line integral is processed at step 422 and reconstructed at step 425 to generate a non-scatter-corrected image 445. These steps 422, 425 may be performed together or in any order. In one embodiment, if steps 422, 425 are performed separately (as depicted in FIG. 4), then each step may utilize an associated filter 423, 426. In another embodiment, if steps 422, 425 are performed together, then only one filter 426 may be utilized. As mentioned above, processing may be performed before, during, and/or after reconstruction in various embodiments. In one embodiment, steps 421, 422, 425 may be associated with an exemplary implementation of step 120.

At step 431, the method generates at least one scatter-only line integral based on the scatter estimate 117. Next, the scatter-only line integral is processed at step 432 and reconstructed at step 435 to generate a scatter-only image 455. These steps 432, 435 may be performed together or in any order. In one embodiment, if steps 432, 435 are performed separately (as depicted in FIG. 4), then each step may utilize an associated filter 433, 436. In another embodiment, if steps 432, 435 are performed together, then only one filter 436 may be utilized. As mentioned above, processing may be performed before, during, and/or after reconstruction in various embodiments. In one embodiment, steps 431, 432, 435 may be associated with an exemplary implementation of step 130.

As discussed above, in various embodiments, one or more filters 433 436 is different than one or more filters 423, 426, where the filters and their associated parameters can be specifically directed to the associated data 115, 117. As discussed above in detail, the filters can be separately optimized for the source data 115, 117, independently optimizing the processing (filtering) of the two imaging data components (non-scatter-corrected and scatter only, as shown in equation 7).

In some embodiments, the non-scatter-corrected line integral from step 421, before or after processing, can be used to guide the processing, for example, with filter 433 and/or filter 436 (e.g., to determine the filter kernel for noise reduction), of the relatively high noise scatter-only data. As discussed above, since the non-scatter corrected data has much lower noise level than the scatter-only data, it can be used to guide the noise reduction of the scatter-only data.

At step 460, the method generates a patient image based on the non-scatter-corrected image 445 and the scatter-only image 455. For example, the scatter-only image 455 can be added to the non-scatter-corrected image 445 to yield the patient image.

Figure 5:
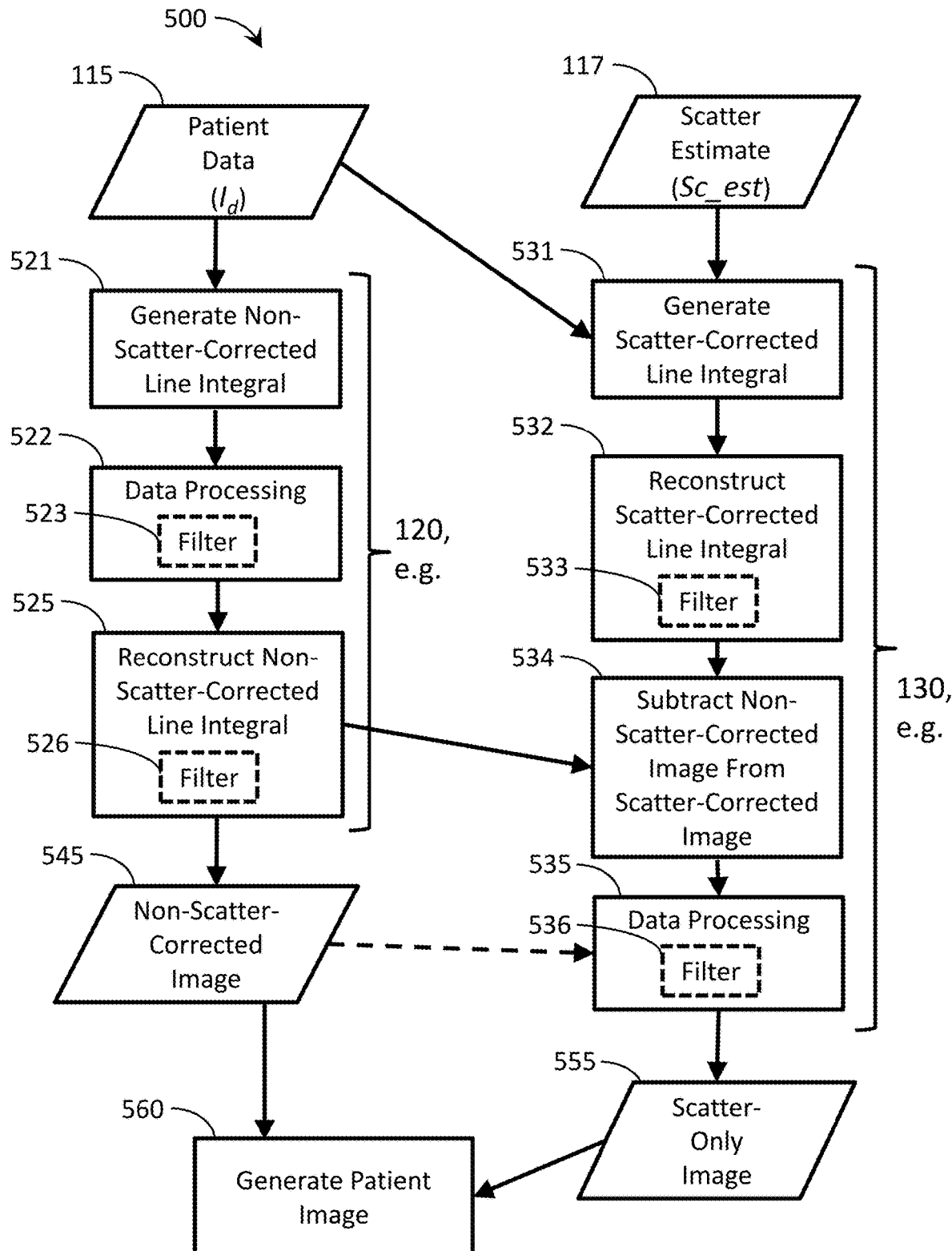
FIG. 5 is a flow chart depicting another exemplary method of generating a radiological image by treating the imaging data as a non-scatter-corrected component and a scatter-only component.

FIG. 5 is a flow chart depicting another exemplary method 500 of generating a radiological image by treating the imaging data as a non-scatter-corrected component and a scatter-only component. In this embodiment, radiation/patient data ($I_d$) 115 and scatter estimate (Sc_est) 117 may be generated as described in method 100, including via a patient scan 110.

At step 521, the method generates at least one non-scatter-corrected line integral based on the patient data 115. Next, the non-scatter-corrected line integral is processed at step 522 and reconstructed at step 525 to generate a non-scatter-corrected image 545. These steps 522, 525 may be performed together or in any order. In one embodiment, if steps 522, 525 are performed separately (as depicted in FIG. 5), then each step may utilize an associated filter 523, 526. In another embodiment, if steps 522, 525 are performed together, then only one filter 526 may be utilized. As mentioned above, processing may be performed before, during, and/or after reconstruction in various embodiments. In one embodiment, steps 521, 522, 525 may be associated with an exemplary implementation of step 120.

At step 531, the method generates at least one scatter-corrected line integral based on the patient data 115 and the scatter estimate 117. Next, the scatter-corrected line integral is reconstructed at step 532. A filter 533 may be utilized before, during, or after reconstruction. Then, at step 534, the method determines a difference between the reconstructed non-scatter-corrected line integral from step 525 and the reconstructed scatter-corrected line integral from step 532. For example, in one embodiment, the non-scatter-corrected image is subtracted from the scatter-corrected image to yield scatter-only image data. Then, at step 535, the difference can be processed using filter 536 to generate a scatter-only image 555. In one embodiment, steps 531, 532, 534, 535 may be associated with an exemplary implementation of step 130.

As discussed above, in various embodiments, one or more filters 533 536 is different than one or more filters 523, 526, where the filters and their associated parameters can be specifically directed to the associated data 115, 117. As discussed above in detail, the filters can be separately optimized for the source data 115, 117, independently optimizing the processing (filtering) of the two imaging data components (non-scatter-corrected and scatter only, as shown in equation 7).

In some embodiments, the non-scatter-corrected image 545, before or after processing, can be used to guide the processing, for example, with filter 536 (i.e., to determine the filter kernel, e.g., for noise reduction), of the relatively high noise scatter-only image/data. As discussed above, since the non-scatter corrected image/data has much lower noise level than the scatter-only image/data, it can be used to guide the noise reduction of the scatter-only image at step 535.

At step 560, the method generates a patient image based on the non-scatter-corrected image 545 and the scatter-only image 555. For example, the scatter-only image 555 can be added to the non-scatter-corrected image 545 to yield the patient image.

Figure 6:
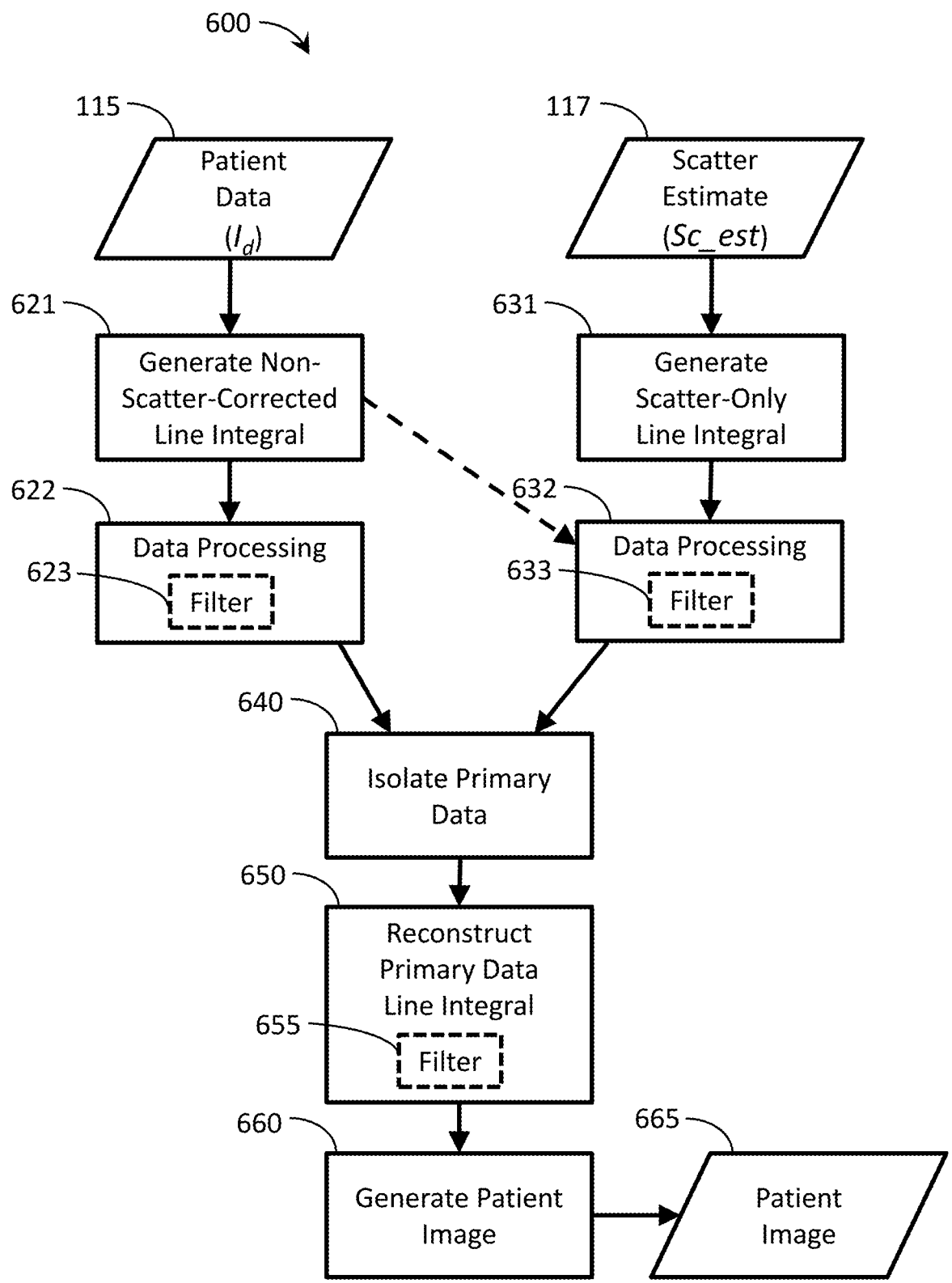
FIG. 6 is a flow chart depicting another exemplary method of generating a radiological image by treating the imaging data as a non-scatter-corrected component and a scatter-only component.

FIG. 6 is a flow chart depicting another exemplary method 600 of generating a radiological image by treating the imaging data as a non-scatter-corrected component and a scatter-only component. In this embodiment, radiation/patient data ($I_d$) 115 and scatter estimate (Sc_est) 117 may be generated as described in method 100, including via a patient scan 110.

At step 621, the method generates at least one non-scatter-corrected line integral based on the patient data 115. Next, the non-scatter-corrected line integral is processed at step 622 using filter 623. At step 631, the method generates at least one scatter-only line integral based on the scatter estimate 117. Next, the scatter-only line integral is processed at step 632 using filter 633.

As discussed above, in various embodiments, one or more filters 633 is different than one or more filters 623, where the filters and their associated parameters can be specifically directed to the associated data 115, 117. As discussed above in detail, the filters can be separately optimized for the source data 115, 117, independently optimizing the processing (filtering) of the two imaging data components (non-scatter-corrected and scatter only, as shown in equation 7).

In some embodiments, the non-scatter-corrected line integral from step 621, before or after processing, can be used to guide the processing, for example, with filter 633 (i.e., to determine the filter kernel, e.g., for noise reduction), of the relatively high noise scatter-only data. As discussed above, since the non-scatter corrected data has much lower noise level than the scatter-only data, it can be used to guide the noise reduction of the scatter-only data.

Then, at step 640, the method isolates the primary data, for example, by determining a difference between the non-scatter-corrected line integral from steps 621, 622 and the scatter-only line integral from steps 631, 632. For example, in one embodiment, the scatter-only line integral data is added to the non-scatter-corrected line integral data to yield the primary-only line-integra data. Then, at step 650, the primary line integral data can be reconstructed, including using filter 655. At step 660, the method generates a patient image 665.

FIGS. 7-11 demonstrate the performance of implementing an exemplary embodiment for a cone-beam CT scan of a pelvic phantom. As compared to a conventional approach with a post-reconstruction low pass filter, the results of this example show much improved bone boundaries (edges in the image) preservation and similar noise reduction. Also, the noise pattern is much more natural than the low-pass filter image.

Figures 7A, 7B, 7C:
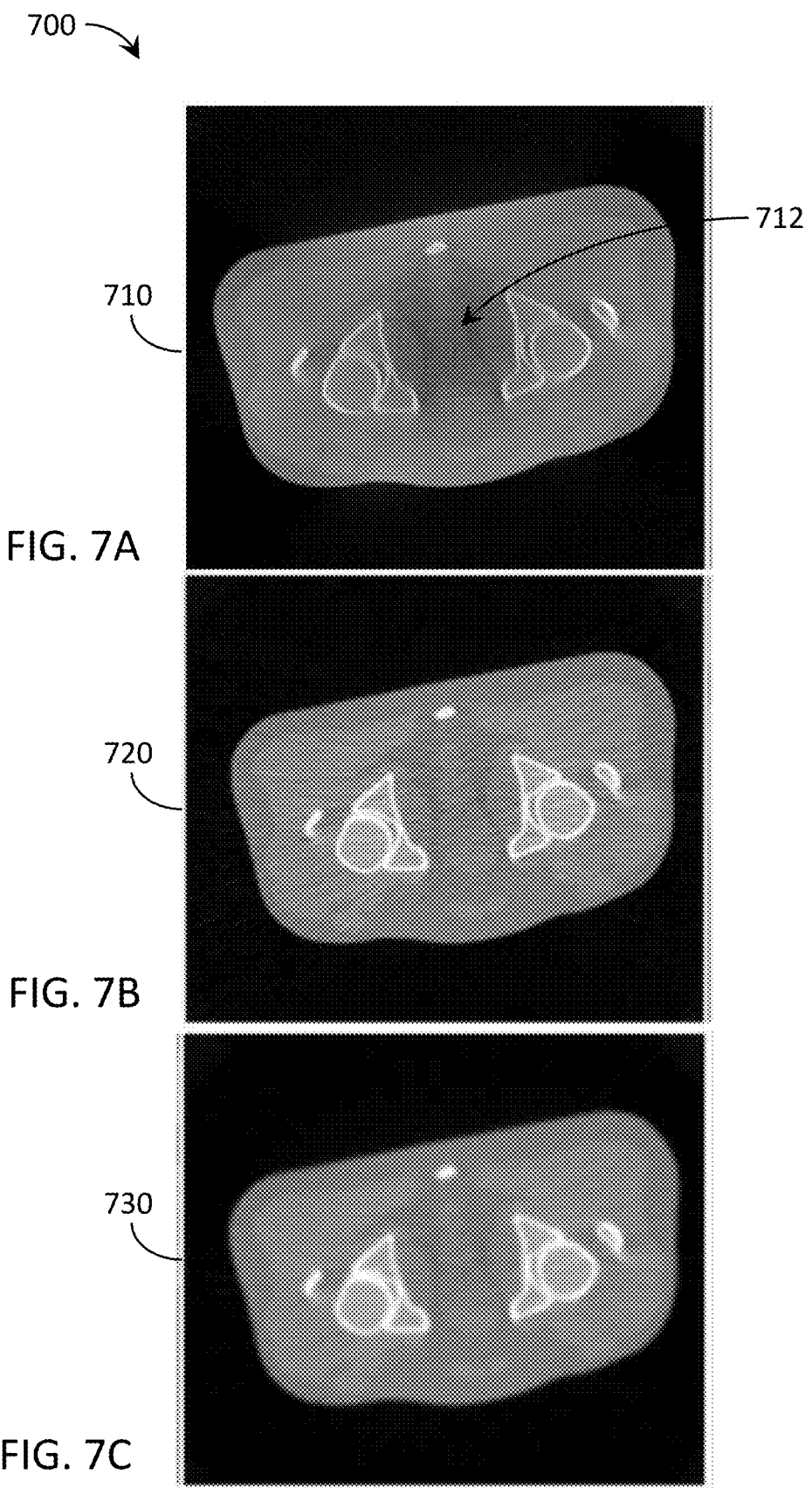
FIG. 7A is an exemplary image generated with no scatter correction.
FIG. 7B is an exemplary image generated with scatter correction.
FIG. 7C is an exemplary image generated with scatter correction followed by a Gaussian low-pass filter.

In particular, FIGS. 7A-7C are cone-beam CT images 700 of a pelvic phantom acquired with collimator aperture ~10 cm at isocenter, 125 kVp, 2.5 mAs, 360 views/rotation, and 24 views per second. FIGS. 7A-7C demonstrate the image quality achieved with conventional image processing that does not utilize the two-component image processing techniques described above (i.e., processing a non-scatter-corrected component and a scatter-only component separately with individualized filters, as shown in the methods above).

FIG. 7A is an image 710 with no scatter correction. FIG. 7B is an image 720 with scatter correction. FIG. 7C is an image 730 with scatter correction followed by a Gaussian low-pass filter. As shown in these images, the scatter correction employed in image 720 minimized the cupping artifact 712 (i.e., dipping of intensity in the middle of the phantom as compared to the peripheral of the phantom in image 710), but image noise was amplified and streak artifacts were introduced throughout image 720. Post-reconstruction processing using a low-pass filter in image 730 reduced the noise and amplitude of the streak artifacts, but sacrificed the image resolution (e.g., visibly blurred bone boundaries).

Figure 8A:
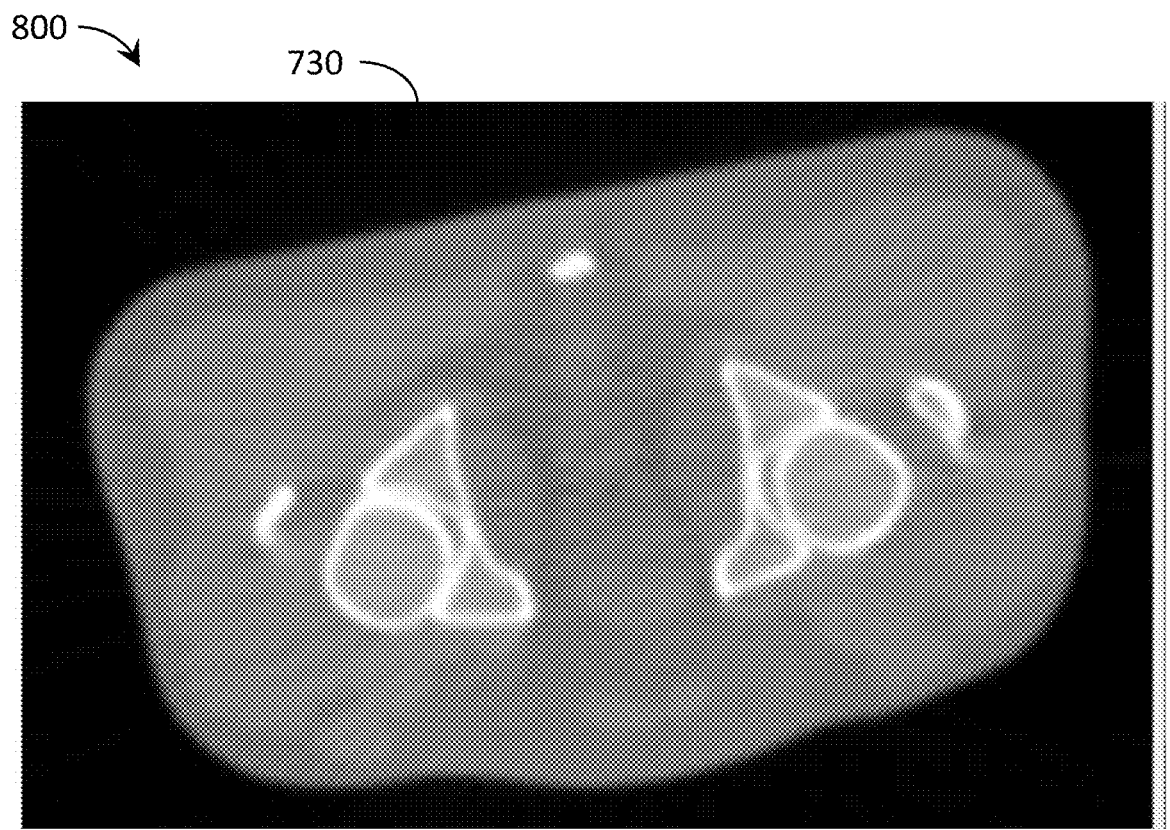
FIG. 8A is a larger view of the exemplary image from FIG. 7C.
Figure 8B:
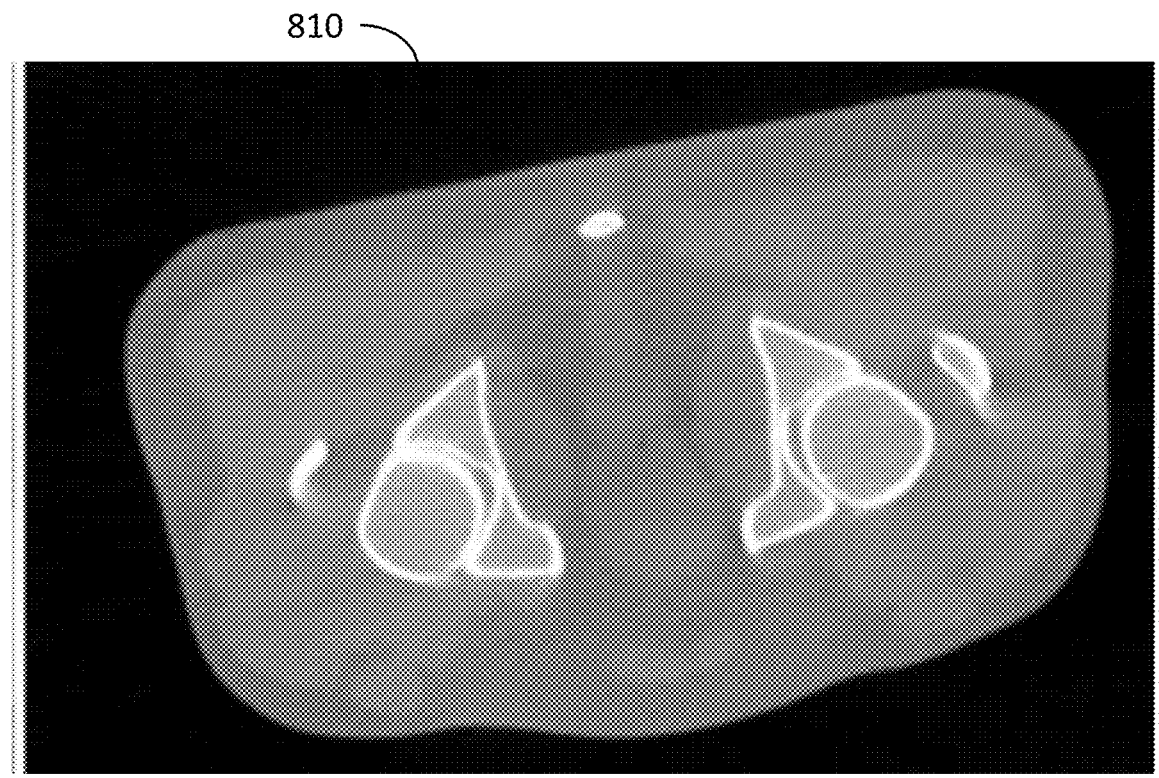
FIG. 8B is an exemplary image generated by treating the imaging data as a non-scatter-corrected component and a scatter-only component.

FIGS. 8A-8B show a comparison 800 of the image quality achieved with conventional image processing versus the exemplary embodiment implementing the two-component image processing techniques described above (i.e., processing a non-scatter-corrected component and a scatter-only component separately with individualized filters). In particular, FIG. 8A is a larger view of image 730 from FIG. 7C, which used conventional scatter correction followed by a Gaussian low-pass filter. FIG. 8B is an image 810 of the same pelvic phantom utilizing method 200 above, which shows noise and artifact reduction and improved edge preservation performance as compared to the Gaussian filtered image 730.

In particular, to generate image 810, the Scatter-only image was processed (filtered) based on the noSC image (e.g., 245 in FIG. 2), where the noSC image is utilized as a guiding image to determine or calculate the filtering kernel. As in method 200, the Scatter-only image was processed (filtered) using a filter different than the filter utilized for the noSC image. In this embodiment, the filtering kernel is a local Gaussian kernel with a size of 7×7×7 and the weight of each voxel is computed using the HU difference of the voxel to the central voxel in the noSC image. The edge information in the noSC image is naturally incorporated into the filter (kernel) computation for the Scatter-only image to preserve the corresponding edges in the Scatter-only image. The resulting image 810 demonstrates effective edge preservation as well as noise and artifact reduction.

Figure 9:
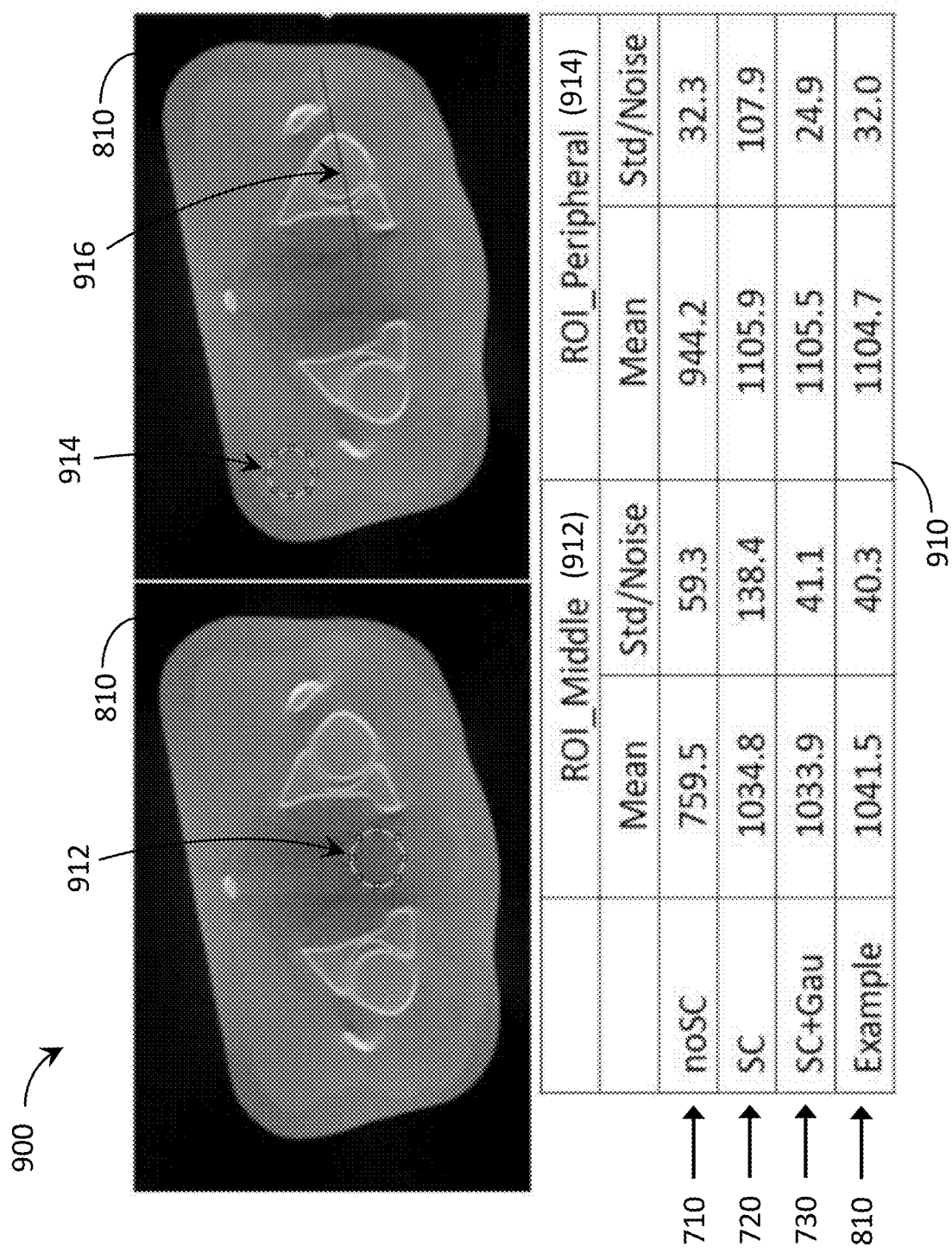
FIG. 9 shows a comparison of exemplary noise measurements associated with the exemplary images from FIGS. 7A-7C and 8B.

FIG. 9 shows a comparison 900 of noise measurements associated with images 710, 720, 730, 810. In particular, mean levels and noise measurements from different regions-of-interest (ROI) for the differently processed images 710, 720, 730, 810 are included in table 910. Note that the mean values in table 910 are the CT numbers plus 1000. The noSC noise data, SC noise data, and SC+Gau noise data are associated with the three images 710, 720, 730 shown in FIGS. 7A-7C, respectively. The "Example" noise data are associated with the image 810 shown in FIG. 8B. The regions of interest include a ROI_Middle 912, ROI_Peripheral 914, and a line profile 916 (detailed in FIG. 10). The noise level of image 810 is similar to the noSC image 710 in the ROI_Peripheral 914 and lower than the noSC image 710 in the ROI_Middle 912. The SC+Gau image 730 has similar noise as the image 810 in the ROI_Middle 912, but lower noise in the ROI_Peripheral 914. However, as is shown in FIG. 8, the SC+Gau image 730 has very strong residual streak artifacts, which are minimal in the image 810. The line profile 916 is used for a line profile comparison shown in FIG. 10.

Figure 10:
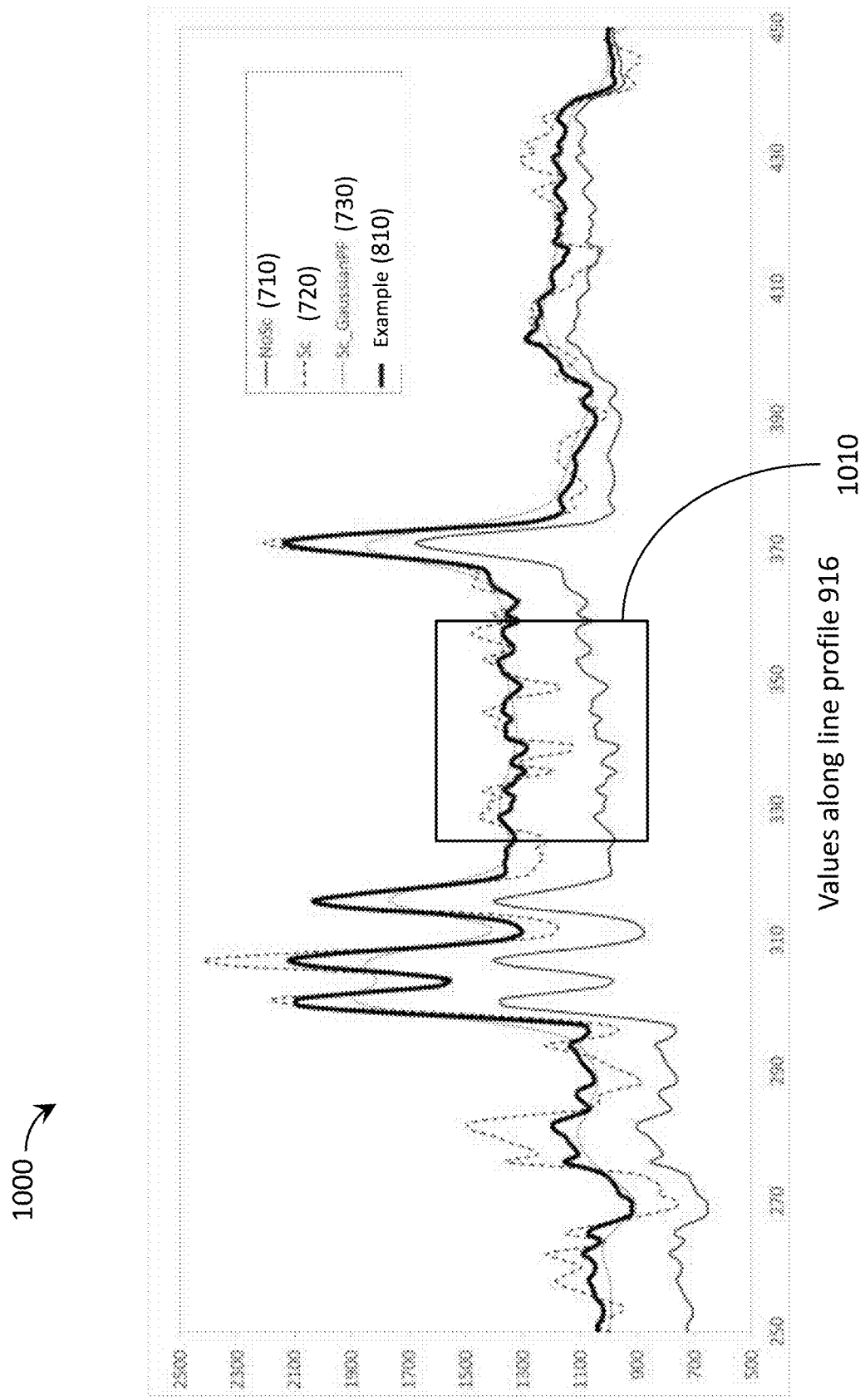
FIG. 10 shows a comparison of exemplary line integral values associated with the exemplary images from FIGS. 7A-7C and 8B along a line profile shown in FIG. 9.
Figure 11:
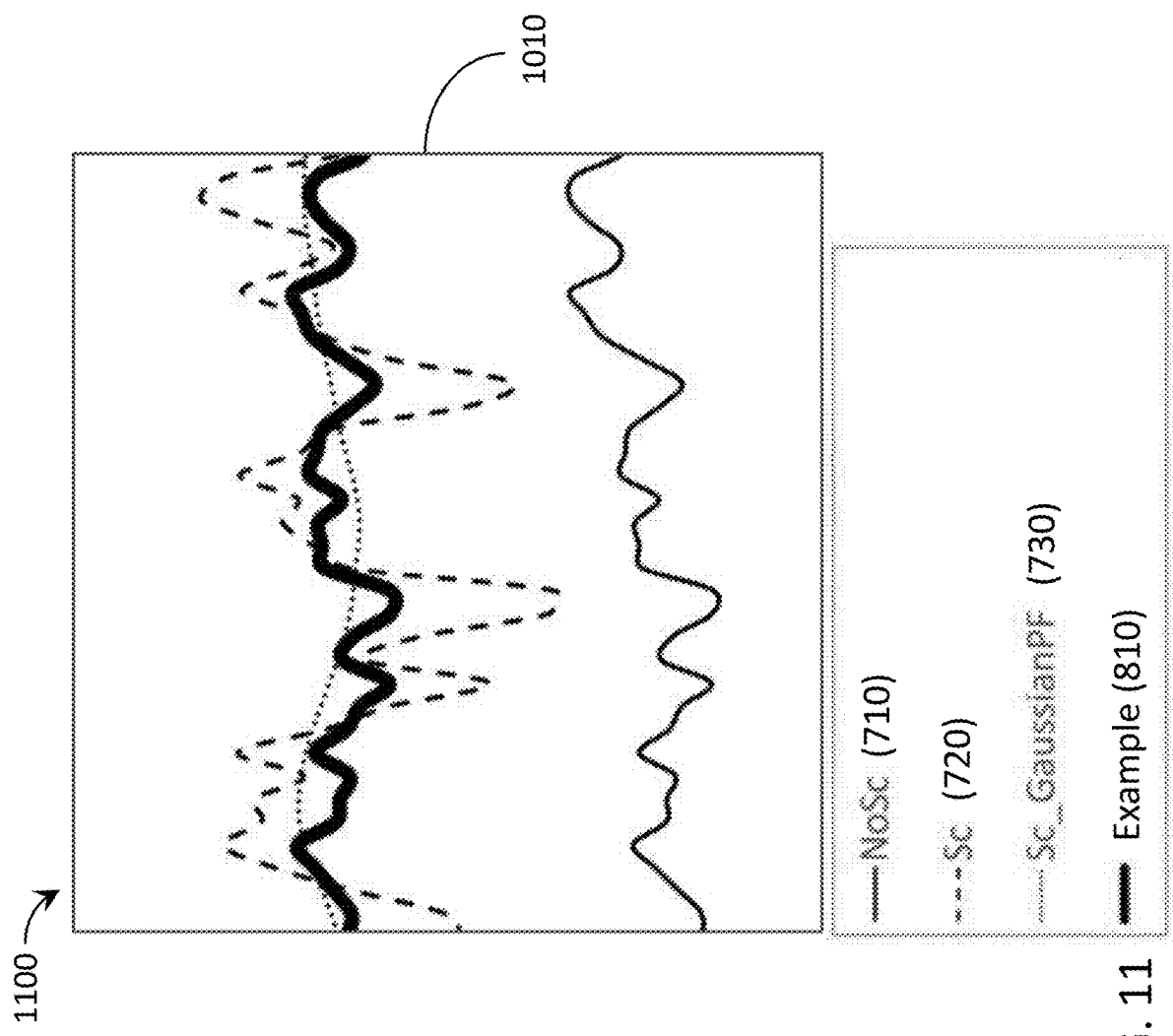
FIG. 11 shows an exploded view of a section of line integral values shown in FIG. 10.

FIG. 10 shows a comparison 1000 of line integral values associated with images 710, 720, 730, 810 along line profile 916. Note that the values in the line integral are the CT number plus 1000. The "NoSc" line, "Sc" line, and "Sc_GaussianPF" line are associated with the line profile 916 through the three images 710, 720, 730 shown in FIGS. 7A-7C, respectively. The "Example" line is associated with the line profile 916 through image 810 shown in FIG. 8B. FIG. 11 shows an exploded view 1100 of section 1010 of the data. The line profiles further demonstrate the effectiveness of the exemplary embodiment in both noise and streak artifact suppression and edge preservation. For example, the Sc line has exaggerated peaks and valleys when compared to the noSc line. Also, the Sc_GaussianPF line is overly smooth in these areas. In contrast, the Example line has the scatter component removed, but without the associated noise, artifacts, loss of resolution, etc.

Figure 12:
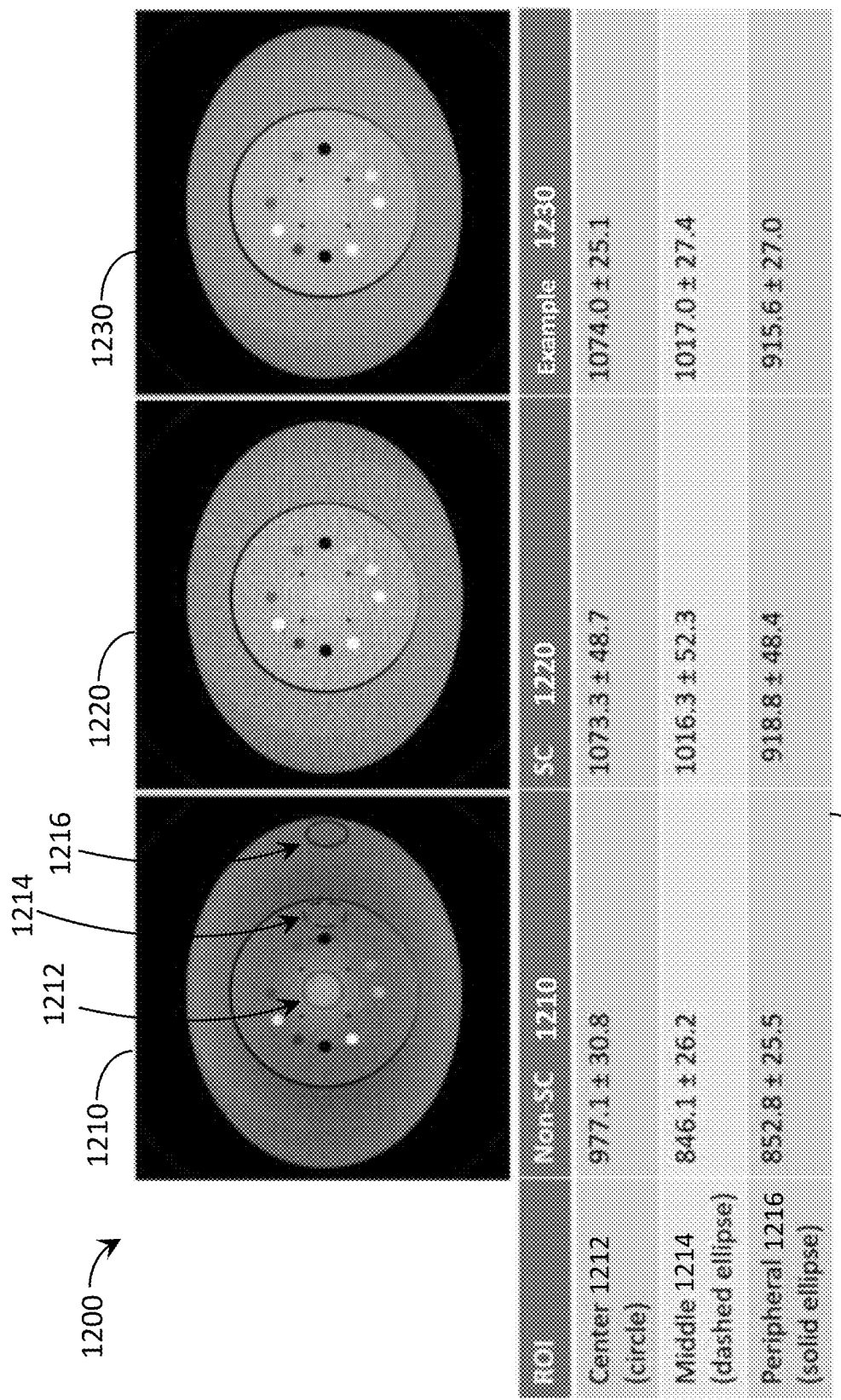
FIG. 12 shows a comparison of exemplary images and CT values associated with conventional image processing and an exemplary embodiment of treating the imaging data as a non-scatter-corrected component and a scatter-only component.

FIG. 12 shows a comparison 1200 of images and CT values associated with conventional image processing and an exemplary embodiment of the two-component image processing techniques described above in a Catphan scan with annulus. This comparison 1200 demonstrates significant noise reduction while the small object boundaries are preserved (visual assessment). Image 1210 (Non-SC) is with no scatter correction. Image 1220 (SC) is with scatter correction. Image 1230 (Example) is scatter corrected in accordance with the two-component method described above. To generate the images, a Catphan plus annulus scan was implemented with an aperture of 4.5 cm at the isocenter. Images 1210, 1220, 1230 are displayed with HU window [−400, 200]. Scan parameters were 125 kV, 2.5 mAs, 480 views/rotation, and 24 frames per second. Table 1250 shows mean CT values+/−standard deviation in ROI 1212 (center—shown as a circle), ROI 1214 (middle—shown as a dashed ellipse), and ROI 1216 (peripheral—shown as a solid ellipse), where the mean value is the CT number plus 1000. Image 1230 (Example), utilizing the exemplary embodiment, has much more suppressed noise when compared to the scatter correction image 1220 (SC). The small contrast boundary and contrast are visually the same in the two images 1220, 1230.

As is discussed in detail above, embodiments of the disclosed technology relate to correcting scatter in imaging data, including utilizing patient data ($I_d$) and a scatter estimate (Sc_est) from an imaging scan. The imaging scan may be performed by any radiological imaging apparatus associated with the type of scan, including x-ray, CT, CBCT, SPECT, PET, MR, etc. These methods can be used for scatter correction in the imaging data from these imaging scans, for example, for noise and artifact reduction. Although CT scanners and cone-beam CT scanners are highlighted in several exemplary embodiments, this technique can also be applied to image reconstruction/data processing based on the removal of unwanted counts/signals from the original counts to generate corrected images, such as, for example, scatter correction in SPECT, PET, MR, SPECT/CT, PET/CT, PET/MR, etc.

In various embodiments, the imaging scan may be performed using a dedicated imaging apparatus or an imaging apparatus integrated with a radiotherapy delivery apparatus. For example, a radiotherapy delivery device can make use of an integrated low-energy radiation source for CT for use in conjunction with or as part of IGRT. In particular, for example, a radiotherapy delivery device and associated methods can combine a low-energy collimated radiation source for imaging in a gantry using rotational (e.g., helical or step-and-shoot) image acquisition along with a high-energy radiation source for therapeutic treatment, as described in U.S. patent application Ser. No. 16/694,145, entitled "MULTIMODAL RADIATION APPARATUS AND METHODS," filed Nov. 25, 2019, and in U.S. patent application Ser. No. 16/694,148, entitled "APPARATUS AND METHODS FOR SCALABLE FIELD OF VIEW IMAGING USING A MULTI-SOURCE SYSTEM," filed Nov. 25, 2019, both of which are incorporated by reference herein in their entirety. In these embodiments, the low-energy radiation source (e.g., kilovolt (kV)) can produce higher quality images than via use of the high-energy radiation source (e.g., megavolt (MV)) for imaging.

The imaging data acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the imaging apparatus collimates a radiation source, including, for example, into a cone beam or a fan beam using, for example, a beamformer. In one embodiment, the collimated beam can be combined with a gantry that continuously rotates while the patient moves, resulting in a helical image acquisition.

Detectors (with various row/slice sizes, configurations, dynamic range, etc.), scan pitch, and/or dynamic collimation are additional features in various embodiments, including to selectively expose portions of the detector and selectively define active readout areas, as discussed in detail below.

The imaging apparatus and method can provide selective and variable collimation of a radiation beam emitted by the source of radiation, including adjusting the radiation beam shape to expose less than the entire active area of an associated radiation detector (e.g., a radiation detector positioned to receive radiation from the radiation source).

Exposing only a primary region of the detector to direct radiation allows shadowed regions of the detector to receive only scatter. Scatter measurements in the shadow region (and in some embodiments measurements in the penumbra region) of the detector can be used to estimate scatter in the primary region of the detector receiving projection data.

Figure 13:
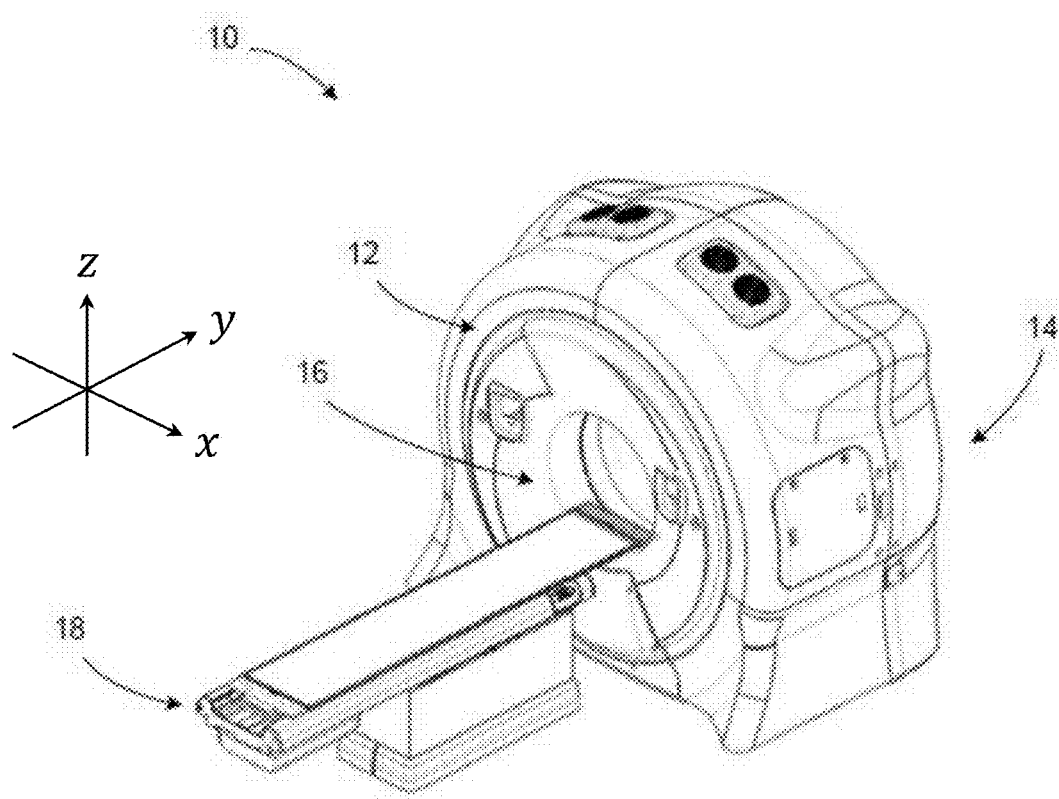
FIG. 13 is a perspective view of an exemplary imaging apparatus in accordance with one aspect of the disclosed technology.
Figure 14:
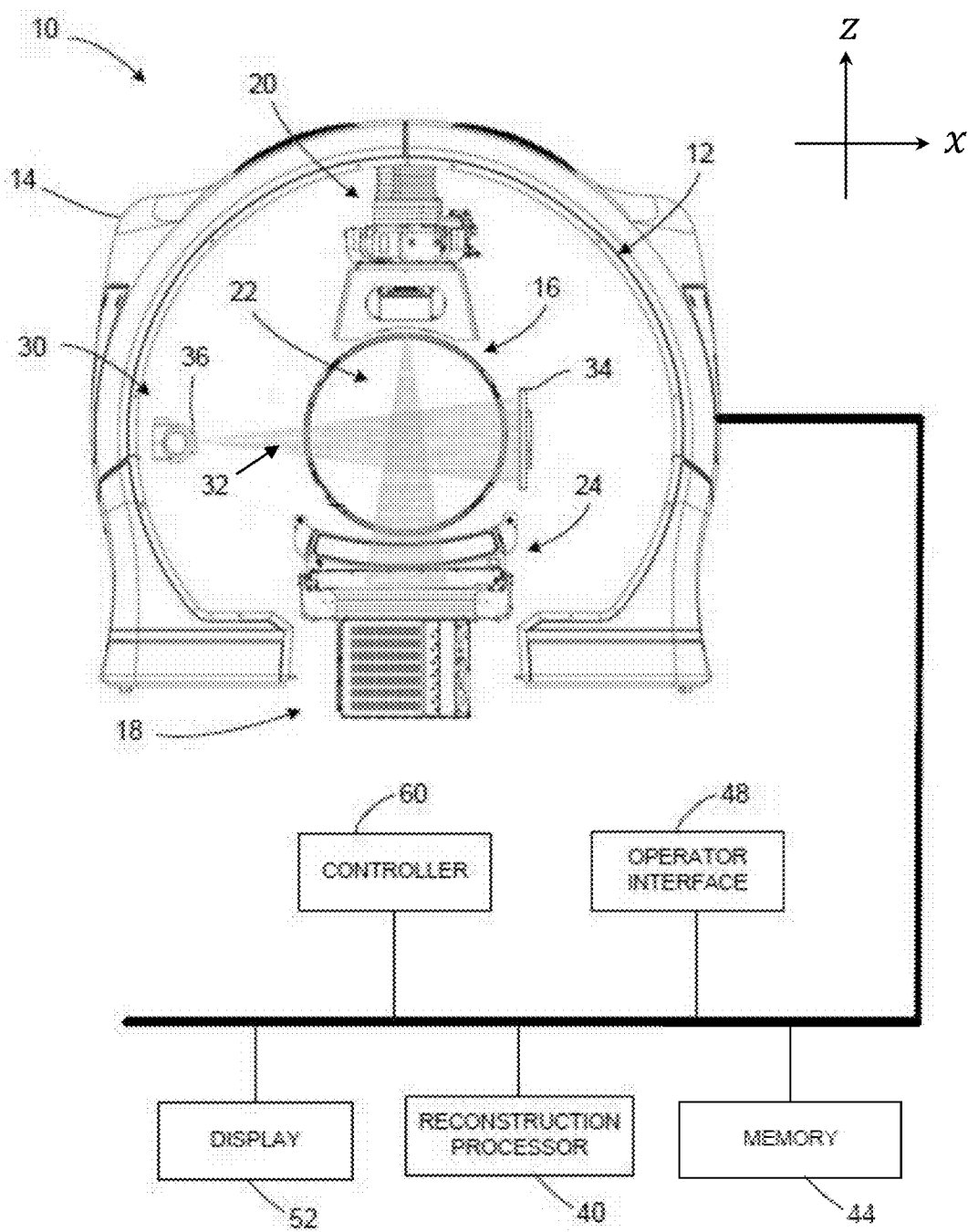
FIG. 14 is a diagrammatic illustration of an imaging apparatus integrated into an exemplary radiotherapy device in accordance with one aspect of the disclosed technology.

With reference to FIGS. 13 and 14, an exemplary imaging apparatus 10 (which can include, e.g., an x-ray imaging apparatus) is shown. It will be appreciated that the imaging apparatus 10 may be associated with and/or integrated into a radiotherapy device (as shown in FIG. 14) that can be used for a variety of applications, including, but not limited to IGRT. The imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of an imaging radiation source (x-ray) and an associated radiation detector while providing sufficient bandwidth for the high-quality imaging data received by the detector.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The apparatus 10 is capable of volume-based and planar-based imaging acquisitions. For example, in various embodiments, the device 10 may be used to acquire volume images and/or planar images and execute the associated processing methods described above.

As shown in FIG. 14, the imaging apparatus 10 includes a source of imaging radiation 30 coupled to or otherwise supported by the rotatable gantry 12. The source of imaging radiation 30 emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). The imaging radiation source can be any type of transmission source suitable for imaging. Other imaging transmission sources can be used interchangeably in various other embodiments.

The imaging apparatus 10 also can include another source of radiation 20 coupled to or otherwise supported by the rotatable gantry 12. In accordance with one embodiment, the source of radiation 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam). Generally, the source of radiation 20 has a higher energy level (peak and/or average, etc.) than the source of imaging radiation 30. Although FIGS. 13 and 14 depict an x-ray imaging apparatus 10 with a radiation source 30 mounted to a ring gantry 12, other embodiments may include other types of rotatable imaging apparatuses, including, for example, C-arm gantries and robotic arm-based systems.

A detector 34 (e.g., two-dimensional flat detector or curved detector) can be coupled to or otherwise supported by the rotatable gantry 12. The detector 34 (e.g., x-ray detector) is positioned to receive radiation from the source of imaging radiation 30 and can rotate along with the source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the radiation source 30 rotates around and emits radiation toward the patient.

A collimator or beamformer assembly (indicated generally as 36) is positioned relative to the imaging source 30 to selectively control and adjust a shape of a radiation beam 32 emitted by the source 30 to selectively expose a portion or region of the active area of the detector 34. The beamformer can also control how the radiation beam 32 is positioned on the detector 34. For example, in one embodiment, 3-4 centimeters of projection image data may be captured with each readout, with about 1-2 centimeters of unexposed detector area on one or each side, which may be used to capture scatter data.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

When integrated with a radiotherapy device, imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, x-ray, CT, CBCT, MR, PET, SPECT, and/or 3D rotational angiography (3DRA) data, and/or any information obtained from these or other imaging modalities. In some embodiments, the imaging apparatus 10 can track in-treatment patient, target, or ROI motion.

A reconstruction processor 40 can be operatively coupled to detectors 24, 34. In one embodiment, the reconstruction processor 40 is configured to generate patient images based on radiation received by detectors 24, 34 from the radiation sources 20, 30, as discussed above. It will be appreciated that the reconstruction processor 40 can be configured to carry out the methods described herein. The apparatus 10 can also include a memory 44 suitable for storing information, including, but not limited to, data processing and reconstruction algorithms and software, including filters and data processing/filter parameters, imaging parameters, image data from a prior or otherwise previously-acquired image (e.g., a planning image), treatment plans, and the like.

The imaging apparatus 10 can include an operator/user interface 48, where an operator of the imaging apparatus 10 can interact with or otherwise control the imaging apparatus 10 to provide input relating to scan or imaging parameters and the like. The operator interface 48 can include any suitable input devices, such as a keyboard, mouse, voice-activated controller, or the like. The imaging apparatus 10 can also include a display 52 or other human-readable element to provide output to the operator of the imaging apparatus 10. For example, the display 52 can allow the operator to observe reconstructed patient images and other information, such as imaging or scan parameters, related to operation of the imaging apparatus 10.

As shown in FIG. 14, the imaging apparatus 10 includes a controller (indicated generally as 60) operatively coupled to one or more components of the apparatus 10. The controller 60 controls the overall functioning and operation of apparatus 10, including providing power and timing signals to the imaging source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the imaging source 30, a beamformer 36 controller, a controller coupled to the detector 24 and/or the detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, an imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with imaging apparatus 10.

Imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

There are many determinants of image quality (e.g., imaging source focal spot size, detector dynamic range, etc.). A limitation of many imaging techniques and image quality is scatter. Various approaches can be used to reduce scatter. One approach is to use an anti-scatter grid (which collimates the scatter). However, it can be problematic to implement a scatter grid on a kV imaging system, including for motion tracking and correction. As discussed above, accurately estimating scatter in the projection data is necessary to improve the quality of the image data. In various embodiments, scatter in the projection data acquired in a primary region of the detector 34 can be estimated based on data measured in shadow regions (and penumbra regions) of the detector 34.

Figure 15:
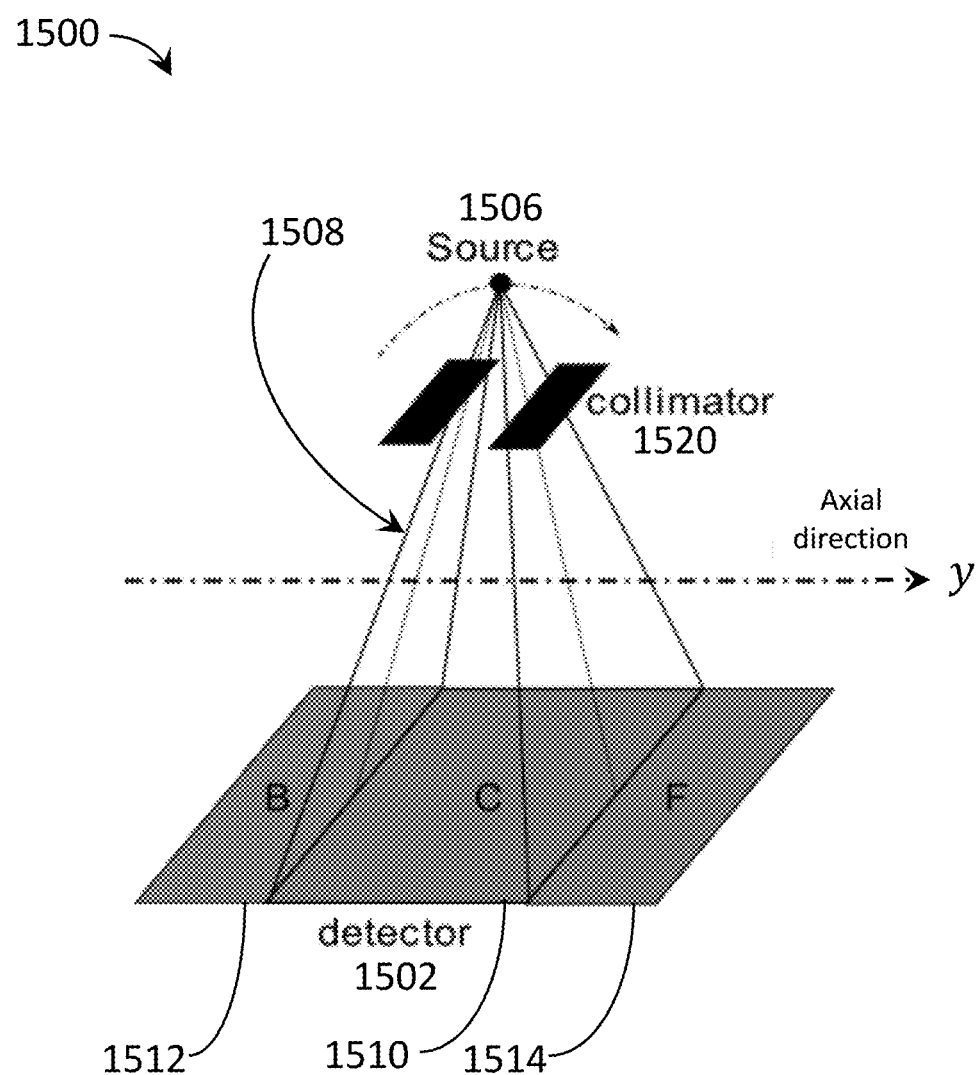
FIG. 15 is a diagrammatic illustration of an exemplary collimated projection onto a detector.

FIG. 15 is a diagrammatic illustration of an exemplary collimated projection 1500 onto a detector 1502. Rotating radiation source 1506 (e.g., x-ray) is shown emitting radiation beam 1508 exposing a primary or center (C) region 1510 of the detector 1502 to direct radiation from source 1506 (e.g., through a target) as the source 1506 rotates around the y-axis. Patient support (not shown) motion can be in an axial (longitudinal) direction along the y-axis, including as part of a scan as described above. Detector 1502 also has a back (B) shadow region 1512 and a front (F) shadow region 1514 that are blocked from direct exposure to the radiation beam 1508 by a beamformer/collimator 1520. Beamformer/collimator 1520 is configured to adjust a shape and/or position of the radiation beam 1508 emitted by the source 1506 onto detector 1502. The shadowed regions 1512, 1514 will only receive scattered radiation.

The collimator 1520 opening is configured in such a way that the back (B) end 1512 and the front (F) end 1514 of the detector 1502 in the axial or longitudinal direction (along the patient table direction or y-axis) are not illuminated with direct radiation 1508. These back (B) 1512 (in the negative longitudinal direction along the rotation y-axis) and front (F) 1514 (in the positive longitudinal direction along the rotation y-axis) shadow regions can be utilized for scatter measurement since they do not receive direct radiation. For example, a detector 1502 readout range can be configured to read out all or a portion of the data in the one or more shadow regions 1512, 1514 and use the data for scatter estimation in the primary region 1510. The primary or center (C) region 1510 receives both direct projections and scatter.

In various embodiments, a data processing system (including, e.g., processor 40) can be configured to receive measured projection data in the primary region 1510 and measured scatter data in at least one shadow region 1512, 1514, then determine an estimated scatter in the primary region 1510 based on the measured scatter data in at least one shadow region 1512, 1514. In some embodiments, determining the estimated scatter in the primary region 1510 during a current rotation can be based on the measured scatter data in at least one shadow region 1512, 1514 during the neighboring (previous and/or subsequent) rotations. In other embodiments, measured data from penumbra region(s) (bordering the primary and shadow regions) may also be used for scatter estimation.

Various techniques and methods can utilize different scan geometries, detector positioning, and/or beamformer window shapes. In some embodiments, the detector may also be offset in the transverse direction.

Figure 16:
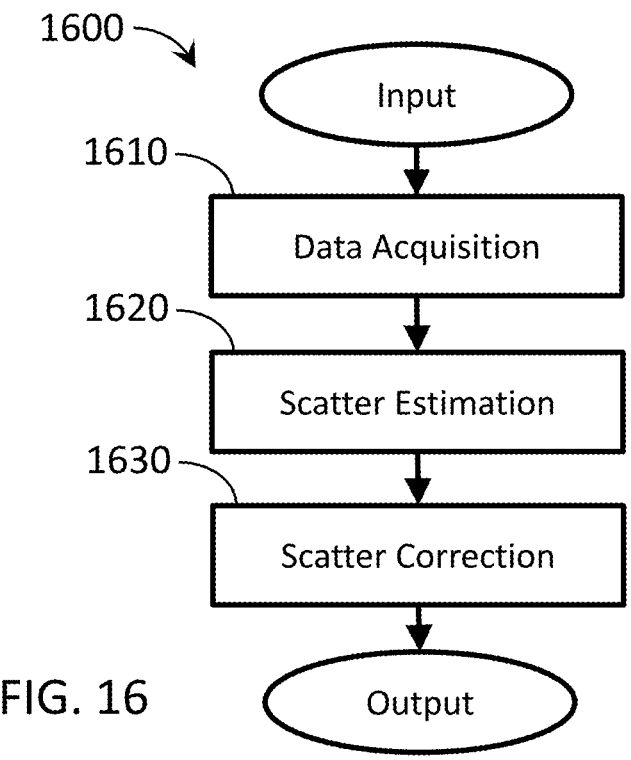
FIG. 16 is a flow chart depicting an exemplary method of scatter correction.

FIG. 16 is a flow chart depicting an exemplary method 1600 of scatter estimation and correction, such as those described above. Inputs can include any optional prior data and/or scan designs. In this embodiment, step 1610 includes data acquisition. For example, during rotation of a radiation source projecting a collimated radiation beam towards a target and radiation detector, the method measures projection data (primary+scatter) in a central (primary) region of a radiation detector and measures scatter using a front shadow peripheral region and/or a back shadow peripheral region of the detector. Data acquisition in step 1610 can also include adjusting a shape/position of the radiation beam with the beamformer before and/or during the scan and/or adjusting a readout range (including determining the active region).

Next, step 1620 includes scatter estimation. For example, the method estimates the scatter in the projection data from the central (primary) region using the scatter measurement from the shadow region(s). Then, step 1630 includes scatter correction, which can include any of the two-component techniques described above. Output includes scatter corrected projection data suitable for imaging. Various embodiments can utilize different scan geometries, detector positioning/active areas, beamformer positioning/window shapes, etc.

Figure 17:
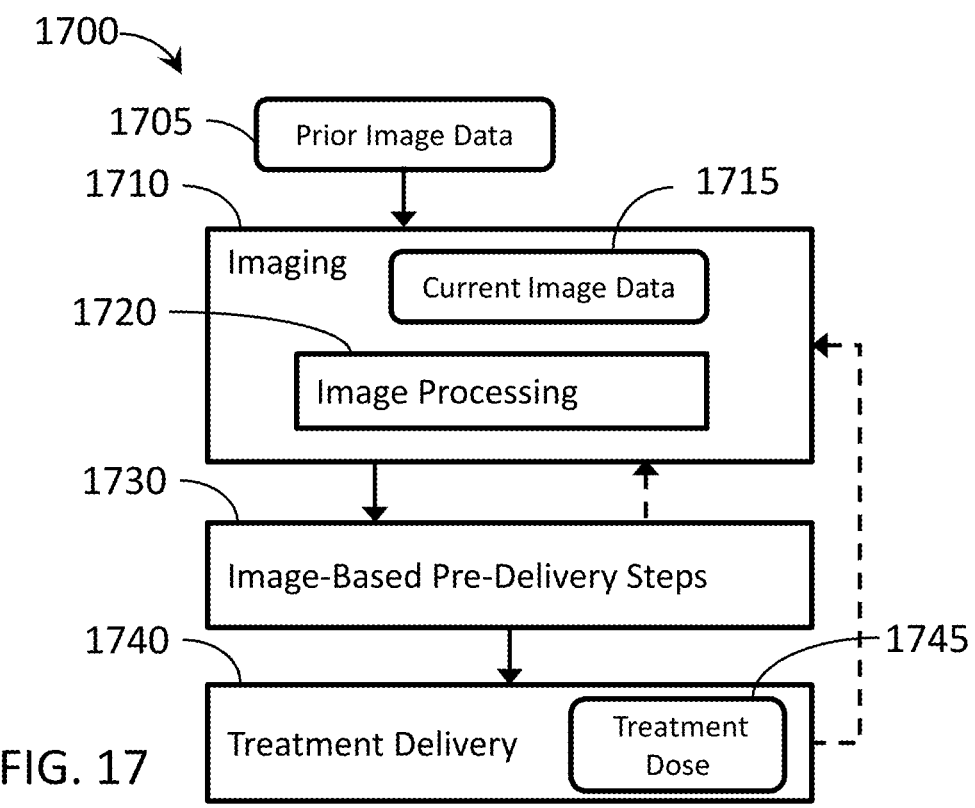
FIG. 17 is a flow chart depicting an exemplary method of IGRT using an imaging apparatus within a radiotherapy device.

FIG. 17 is a flow chart depicting an exemplary method 1700 of IGRT using a radiotherapy device (including, e.g., imaging apparatus 10). Prior image data 1705 of the patient may be available for use, which may be a previously-acquired planning image, including a prior CT image. Prior data 1705 can also include treatment plans, phantom information, models, a priori information, etc. In some embodiments, prior image data 1705 is generated by the same radiotherapy device, but at an earlier time. At step 1710, imaging of a patient is performed using a source of low-energy radiation (e.g., kV radiation from x-ray source 30). In one embodiment, imaging comprises a helical scan with a fan or cone beam geometry. Step 1710 can produce high-quality (HQ) image(s) or imaging data 1715 using the scatter estimation and correction techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1710 can also include image/data processing to generate patient images based on the imaging data (e.g., in accordance with the methods described above). Although image processing step 1720 is shown as part of imaging step 1710, in some embodiments image processing step 1720 is a separate step, including where image processing is executed by separate devices.

Next, at step 1730, one or more image-based pre-delivery steps, discussed below, are performed based at least in part on the imaging data 1715 from step 1710. As discussed in more detail below, step 1730 can include determining various parameters associated with the therapeutic treatment and (subsequent) imaging planning. In some embodiments, image-based pre-delivery steps (1730) may require more imaging (1710) before treatment delivery (1740). Step 1730 can include adapting a treatment plan based on the imaging data 1715 as part of an adaptive radiotherapy routine. In some embodiments, image-based pre-delivery steps 1730 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1740, therapeutic treatment delivery is performed using a source of high-energy radiation (e.g., MV radiation from therapeutic radiation source 20). Step 1740 delivers a treatment dose 1745 to the patient according to the treatment plan. In some embodiments, the IGRT method 1700 may include returning to step 1710 for additional imaging at various intervals, followed by image-based pre-delivery steps (1730) and/or treatment delivery (1740) as required. In this manner the high-quality imaging data 1715 may be produced and utilized during IGRT using one apparatus 10 that is capable of adaptive therapy. As mentioned above, steps 1710, 1720, 1730, and/or 1740 may be executed simultaneously, overlapping, and/or alternating.

In various embodiments, whether the imaging data is generated using a dedicated imaging apparatus or an imaging apparatus integrated with a radiotherapy delivery apparatus, the various methods described above can be utilized for scatter correction.

In one embodiment, a CT apparatus includes a rotating x-ray source and an x-ray detector obtain a set of raw data (e.g., $I_d$) for CT image generation, hardware and/or software to measure and/or generate a set of scatter data (e.g., Sc_est) to compensate/correct the scatter contamination in the raw data. A non-scatter corrected image is reconstructed from the raw data, and a scatter only image is reconstructed from the scatter data. In this embodiment, the raw data can be used to compute non-scatter corrected line integrals for the reconstruction of a non-scatter corrected CT image. The scatter data can be used to compute scatter-only line integrals based on equation 6 for the reconstruction of a scatter-only image. The non-scatter-corrected image and the scatter-only image are processed independently with the latter being filtered more heavily due to the higher noise. The processed non-scatter-corrected image and the processed scatter-only image can be combined to create the final CT image with scatter correction.

In another embodiment, volume image subtraction may be used to generate the scatter-only image. Here, the scatter data is used together with the raw data to generate scatter-corrected line integrals for the reconstruction of a scatter-corrected image. The raw data can be used to compute non-scatter-corrected line integrals to reconstruct a non-scatter-corrected image. The non-scatter corrected image can be subtracted from the scatter-corrected image to obtain the scatter-only image. The non-scatter-corrected image and the scatter-only image are processed independently with the latter being filtered more heavily due to the higher noise. The processed non-scatter-corrected image and the processed scatter-only image can be combined together to create the final CT image with scatter correction.

In various embodiments, the non-scatter-corrected image can be used to guide the processing of the scatter-only image to achieve effective noise and artifact reduction of the scatter-only image while preserving the edges in the image. For example, the filter can be a Gaussian filter that uses the voxel difference in the non-scatter-corrected image to determine the kernel weights of the scatter-only image filter. In this manner, the edge information in the non-scatter-corrected images is used to preserve the corresponding edges in the scatter-only images. The non-scatter-corrected image can also be used in more advanced edge-preserving processing schemes to enhance the processing of the scatter-only image. For example, processing the scatter-only image can be based on the anisotropic differential filter parameters obtained in the non-scatter-corrected images.

In another embodiment, the non-scatter-corrected image and the scatter-only image can be reconstructed using different reconstruction schemes. For example, the non-scatter-corrected image can be reconstructed using a higher resolution kernel than the scatter-only image and the scatter-only image can be reconstructed using a customized streak artifact reduction algorithm. The scatter-only image can be reconstructed using a different grid to speed up the reconstruction time. For example, if the non-scatter-corrected image reconstruction uses a matrix of 512×512, the scatter-only image reconstruction can use a 256×256 matrix for reconstruction to speed up the reconstruction time. The reconstructed scatter-only image can then be resampled to the same grid as the non-scatter-corrected image. The non-scatter-corrected image can then be used to guide the processing of the scatter-only image. The resulting scatter-only image can be combined with the non-scatter-corrected image to create the final image with scatter correction.

In addition to the CT environment highlighted in several of the exemplary embodiments, in various other embodiments, a variety of imaging apparatuses that acquire or generate raw data with scatter (e.g., $I_d$) and the scatter data (e.g., Sc_est), can use the scatter data to correct the raw data, such as in SPECT, PET, etc. Scatter data can be used to modify/correct the line integral where the line integral can be decomposed into a linear combination of the component without scatter correction and the component due to scatter correction similar to equation 6. The non-scatter-corrected image is of lower noise than the scatter-only image. The two images can be reconstructed differently to optimize the quality of both and then can be combined to obtain the final image. The reconstructed non-scatter-corrected image and the scatter-only image can be processed independently to optimize the quality of both and then can be combined to obtain the final image. The non-scatter-corrected image can also be used as a guiding image to determine the weight of filtering kernels when processing the scatter-only image.

In addition to the embodiments that utilize the non-scatter-corrected image to guide the processing of the scatter-only image (i.e., operating in the image domain), other embodiments can operate in the data domain. In these embodiments, processing of the generated line integral of the scatter-only component can be based on the line integral data of the non-scatter-corrected component as the guiding data to preserve the edges in the scatter-only component. The resulting line integral of the scatter-only component can be reconstructed separately or together with the line integral of the non-scatter-corrected component.

In various embodiments, the raw data (e.g., $I_d$) and the measured scatter data (e.g., Sc_est) are used together to reconstruct a scatter-corrected image and the raw data is used to reconstruct a non-scatter-corrected image using various reconstruction algorithms to obtain the images. In some embodiments, the reconstruction can be an analytical reconstruction. In some embodiments, the reconstruction can be an iterative reconstruction. In various embodiments, the scatter only image is processed (including filtering, artifact reduction, etc.) separately from the non-scatter-corrected image, then combined with the non-scatter corrected image to obtain the final image. In some embodiments, a scatter-only image is generated by subtracting the non-scatter-corrected image from the scatter-corrected image. Furthermore, the non-scatter-corrected image can be used to guide the processing of the scatter-only image for optimal noise and artifact reduction and edge preservation.

Generally, in various embodiments, the techniques described above can be applicable to any imaging apparatus and any correction approaches that change the line integral for image reconstruction generate correction terms which changes the line integrals for image reconstruction (e.g., that lead to increased image noise and artifacts). For example, the correction term can be the lag correction term in cone-beam CT using flat panel detectors. Multiple correction terms, such as lag correction and scatter correction in cone-beam CT jointly alter the line integral for reconstruction, while the line integral can be decomposed into the two components, without and with the corrections, similar to that in equation 6. The methods described above can be utilized to obtain the final image with improved quality and performance.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:
1. A radiological imaging apparatus, comprising:
a radiation source for emitting radiation;
a radiation detector positioned to receive radiation from the radiation source and generate radiation data, wherein the radiation data comprises a primary component and a scatter component;
a data processing system configured to:
receive the radiation data;
generate a non-scatter-corrected image based on the radiation data and using a first data processing technique;
estimate the scatter component of the radiation data;
generate a scatter-only image based on the scatter estimate and using a second data processing technique, wherein the second data processing technique is different than the first data processing technique; and
generate an image based on the non-scatter-corrected image and the scatter-only image.

2. The imaging apparatus of claim 1, wherein:
the radiation source comprises a rotating x-ray source emitting a radiation beam;
the radiation detector comprises an x-ray detector positioned to receive the radiation from the x-ray source; and
the apparatus further comprises:
a beamformer configured to adjust a shape of the radiation beam emitted by the x-ray source, such that a primary region of the x-ray detector is directly exposed to the radiation beam and at least one shadow region of the x-ray detector is blocked from direct exposure to the radiation beam by the beamformer.

3. The imaging apparatus of claim 2, wherein estimating the scatter component of the radiation data is based on measured scatter data in the at least one shadow region.

4. The imaging apparatus of claim 1, wherein:
generating the non-scatter-corrected image comprises reconstructing the radiation data; and
generating the scatter-only image comprises:
reconstructing a scatter-corrected image based on the radiation data and the scatter estimate; and
subtracting the non-scatter-corrected image from the scatter-corrected image.

5. The imaging apparatus of claim 1, wherein:
generating the non-scatter-corrected image comprises reconstructing the radiation data, wherein the first data processing technique comprises a higher-resolution kernel than the second data processing technique; and
generating the scatter-only image comprises reconstructing the scatter estimate using a streak artifact reduction algorithm.

6. The imaging apparatus of claim 1, wherein:
generating the non-scatter-corrected image comprises reconstructing the radiation data using a first grid; and
generating the scatter-only image comprises:
reconstructing the scatter-only image using a second grid associated with a faster reconstruction time than the first grid;
resampling the reconstructed scatter-only image using the first grid;

processing the scatter-only image based on a third data processing technique, wherein the third data processing technique is determined based on the non-scatter-corrected image.

7. The imaging apparatus of claim 1, wherein the first data processing technique comprises a high-resolution kernel and the second data processing technique comprises a smoothing kernel.

8. The imaging apparatus of claim 1, wherein the second data processing technique is determined based on the non-scatter-corrected image.

9. The imaging apparatus of claim 1, further comprising processing the scatter-only image based on a third data processing technique, wherein the third data processing technique is determined based on the non-scatter-corrected image.

10. The imaging apparatus of claim 9, wherein the third data processing technique comprises a Gaussian filter that uses a voxel difference in the non-scatter-corrected image to determine kernel weights for the third data processing technique.

11. The imaging apparatus of claim 9, wherein processing the scatter-only image comprises using anisotropic differential filter parameters obtained from the non-scatter-corrected image to process the scatter-only image.

12. The imaging apparatus of claim 1, wherein the first data processing technique is applied to the radiation data before reconstruction of the non-scatter-corrected image and the second data processing technique is applied to the scatter estimate before reconstruction of the scatter-only image.

13. A method of generating a radiological image, comprising:
receiving radiation data from a radiological imaging apparatus, wherein the radiation data comprises a primary component and a scatter component;
generating a non-scatter-corrected data set based on the radiation data and using a first data processing technique;
estimating the scatter component of the radiation data;
generating a scatter-only data set based on the scatter estimate and using a second data processing technique, wherein the second data processing technique is different than the first data processing technique; and
generating an image based on the non-scatter-corrected data set and the scatter-only data set.

14. The method of claim 13, wherein:
generating the non-scatter-corrected data set based on the radiation data and using the first data processing technique comprises:
generating a non-scatter-corrected line integral; and
reconstructing and processing the non-scatter-corrected line integral using the first data processing technique to generate a non-scatter-corrected image;
generating the scatter-only data set based on the scatter estimate and using the second data processing technique comprises:
generating a scatter-only line integral; and
reconstructing and processing the reconstructed scatter-only line integral using the second data processing technique to generate a scatter-only image; and
generating the image based on the non-scatter-corrected data set and the scatter-only data set comprises adding the scatter-only image to the non-scatter-corrected image.

15. The method of claim 14, wherein the second data processing technique is based on the non-scatter-corrected image.

16. The method of claim 13, wherein:
generating the non-scatter-corrected data set based on the radiation data and using the first data processing technique comprises:
generating a non-scatter-corrected line integral; and
reconstructing and processing the reconstructed non-scatter-corrected line integral using the first data processing technique to generate a non-scatter-corrected image;
generating the scatter-only data set based on the scatter estimate and using the second data processing technique comprises:
generating a scatter-corrected line integral;
reconstructing the scatter-corrected line integral;
determining a difference between the reconstructed non-scatter-corrected line integral and the reconstructed scatter-corrected line integral; and
processing the difference using the second data processing technique to generate a scatter-only image; and
generating the image based on the non-scatter-corrected data set and the scatter-only data set comprises adding the scatter-only image to the non-scatter-corrected image.

17. The method of claim 13, wherein:
generating the non-scatter-corrected data set based on the radiation data and using the first data processing technique comprises:
generating a non-scatter-corrected line integral; and
reconstructing and processing the non-scatter-corrected line integral using the first data processing technique to generate a non-scatter-corrected image;
generating the scatter-only data set based on the scatter estimate and using the second data processing technique comprises:
generating a scatter-only line integral; and
reconstructing and processing the scatter-only line integral using the second data processing technique to generate a scatter-only image; and
generating the image based on the non-scatter-corrected data set and the scatter-only data set comprises adding the scatter-only image to the non-scatter-corrected image.

18. The method of claim 13, wherein:
generating the non-scatter-corrected data set based on the radiation data and using the first data processing technique comprises:
generating a non-scatter-corrected line integral; and
reconstructing and processing the non-scatter-corrected line integral using the first data processing technique to generate a non-scatter-corrected image;
generating the scatter-only data set based on the scatter estimate and using the second data processing technique comprises:
generating a scatter-corrected line integral;
reconstructing the scatter-corrected line integral to generate a scatter-corrected image;
determining a difference between the reconstructed non-scatter-corrected line integral and the reconstructed scatter-corrected line integral; and
processing the difference using the second data processing technique to generate a scatter-only image; and
generating the image based on the non-scatter-corrected data set and the scatter-only data set comprises adding the scatter-only image to the non-scatter-corrected image.

19. The method of claim 13, wherein:
generating the non-scatter-corrected data set based on the radiation data and using the first data processing technique comprises:
generating a non-scatter-corrected line integral; and
processing the non-scatter-corrected line integral using the first data processing technique;
generating the scatter-only data set based on the scatter estimate and using the second data processing technique comprises:
generating a scatter-only line integral; and
processing the scatter-only line integral using the second data processing technique; and
generating the image based on the non-scatter-corrected data set and the scatter-only data set comprises:
isolating a primary data line integral based on the difference between the processed non-scatter-corrected line integral and the processed scatter-only line integral;
reconstructing the primary data line integral to generate the image.

20. A radiotherapy delivery device comprising:
a rotatable gantry system positioned at least partially around a patient support;
a first source of radiation coupled to the rotatable gantry system, the first source of radiation being configured as a source of therapeutic radiation;
a second source of radiation coupled to the rotatable gantry system, the second source of radiation being configured as a source of imaging radiation having an energy level less than the source of therapeutic radiation;
a radiation detector coupled to the rotatable gantry system and positioned to receive radiation from the second source of radiation; and
a data processing system configured to:
receive radiation data, wherein the radiation data comprises a primary component and a scatter component;
generate a non-scatter-corrected data set based on the radiation data and using a first data processing technique;
estimate the scatter component of the radiation data;
generate a scatter-only data set based on the scatter estimate and using a second data processing technique, wherein the second data processing technique is different than the first data processing technique;
generate an image based on the non-scatter-corrected data set and the scatter-only data set; and
deliver a dose of therapeutic radiation to the patient via the first radiation source based on the image during adaptive IGRT.

* * * * *